United States Patent
Hirao et al.

(10) Patent No.: US 8,212,014 B2
(45) Date of Patent: Jul. 3, 2012

(54) ARTIFICIAL BASE PAIRS AND USES THEREOF

(75) Inventors: Ichiro Hirao, Yokohama (JP); Michiko Hirao, Yokohama (JP); Shigeyuki Yokoyama, Yokohama (JP)

(73) Assignee: Riken, Wako-shi, Saitama (JP)

( * ) Notice: Subject to any disclaimer, the term of this patent is extended or adjusted under 35 U.S.C. 154(b) by 880 days.

(21) Appl. No.: 11/989,840

(22) PCT Filed: Aug. 4, 2006

(86) PCT No.: PCT/JP2006/315479
§ 371 (c)(1),
(2), (4) Date: Nov. 25, 2008

(87) PCT Pub. No.: WO2007/015557
PCT Pub. Date: Feb. 8, 2007

(65) Prior Publication Data
US 2010/0285598 A1    Nov. 11, 2010

(30) Foreign Application Priority Data

Aug. 4, 2005 (JP) ................. 2005-226492
Jun. 30, 2006 (JP) ................. 2006-182062

(51) Int. Cl.
*C07H 21/00* (2006.01)
*C07H 21/02* (2006.01)
*C12Q 1/68* (2006.01)
*C12P 19/34* (2006.01)

(52) U.S. Cl. .................. 536/23.1; 536/24.3; 536/24.33; 435/6; 435/91.1

(58) Field of Classification Search .................. 536/23.1, 536/24.3, 24.33; 435/6, 91.1
See application file for complete search history.

(56) References Cited

FOREIGN PATENT DOCUMENTS

| EP | 1114827 A1 | 7/2001 |
| EP | 1544294 | 6/2005 |
| EP | 1970445 | 9/2008 |
| WO | WO-01/05801 | 1/2001 |
| WO | WO-2004/007713 | 1/2004 |
| WO | WO-2005/026187 A1 | 3/2005 |

OTHER PUBLICATIONS

Fujiwara, T., et al., "Synthesis of 6-(2-thienyl)purine nucleoside derivatives toward the expansion of the genetic code," Nucleic Acids Symposium Series No. 44, pp. 43-44 (2000).
T. Mitsui et al., Journal of the American Chemical Society, May 7, 2003, vol. 125, No. 18, pp. 5298-5307.
Ichiro Hirao et al., Nucleic Acids Symp Ser, Sep. 2005, vol. 49, p. 33-34.
Ichiro Hirao, Chemistry & chemical industry, Aug. 1, 2006, vol. 59, No. 8, pp. 848-851.

(Continued)

*Primary Examiner* — Jezia Riley
(74) *Attorney, Agent, or Firm* — Birch, Stewart, Kolasch & Birch, LLP

(57) ABSTRACT

The present invention provides nucleic acids based on novel artificial base pairing, as well as a preparation method and uses thereof.
In the nucleic acids of the present invention, a nucleotide having a substituted or unsubstituted 2-formyl-1H-pyrrol-1-yl group as a base forms a base pair with a nucleotide having a 6-substituted 9H-purin-9-yl group as a base. The inventive method for preparing a nucleic acid comprises effecting transcription, reverse transcription or replication by using, as a template, a nucleic acid incorporating a nucleotide having a substituted or unsubstituted 2-formyl-1H-pyrrol-1-yl group as a base, so that the nucleotide having a 6-substituted 9H-purin-9-yl group is incorporated at a site complementary to the nucleotide having a substituted or unsubstituted 2-formyl-1H-pyrrol-1-yl group.

20 Claims, 15 Drawing Sheets

OTHER PUBLICATIONS

Benner, S. A., et al., "Did the RNA World Exploit an Expanded Genetic Alphabet?", The RNA World, 2d Ed., pp. 163-181 (1999).

Bergstrom, D.E., "Orthogonal Base Pairs Continue to Evolve," Chem. & Biol., vol. 11, pp. 18-20 (2004).

Wang, L., et al., "Expanding the genetic code," Chem. Commun., pp. 1-11, (2002).

Hendrickson, T.L., et al., "Incorporation of Nonnatural Amino Acids Into Proteins," Annu. Rev. Biochem, vol. 73, pp. 147-176 (2004).

Morales, J.C., et al., "Efficient replication between non-hydrogen-bonded nucleoside shape analogs," Nat. Struct. Biol., vol. 5, No. 11, pp. 950-954 (1998).

Kool, E.T., "Hydrogen Bonding, Base Stacking, and Steric Effects in DNA Replication," Annu. Rev. Biophys., Biolmol. Sruct., vol. 30, pp. 1-22 (2001).

McMinn, D. L., et al., "Efforts toward Expansion of the Genetic Alphabet: DNA Polymerase Recognition of a Highly Stable, Self-Pairing Hydrophic Base," J. Am. Chem., Soc., vol. 121, pp. 11585-11586 (1999).

Wu, Y., et al., "Efforts toward Expansion of the Genetic Alphabet: Optimization of Interbase Hydrophic Interactions," J. Am. Chem. Soc., vol. 122, No. 32, pp. 7621-7632 (2000).

Mitsui, T., et al., "An Unnatural Hydrophobic Base Pair with Shape Complementarity between Pyrrole-2-carbaldehyde and 9-Methylimidazo[(4,5)-b]pyridine," J. Am. Chem. Soc., vol. 125, pp. 5298-5307 (2003).

Piccirilli, J.A., et al., Enzymatic incorporation of a new base pair into DNA and RNA extends the genetic alphabet, Nature, vol. 343, pp. 33-37 (1990).

Switzer, C. Y., et al., "Enzymatic Recognition of the Base Pair between Isocytidine and Isoguanosine," Biochem., vol. 32, pp. 10489-10498 (1993).

Tor, Y., et al., "Site-specific Enzymatic Incorporation of an Unnatural Base, $N^6$-(6-Aminohexyl)isoguanosine, into RNA," J. Am. Chem. Soc., vol. 115, pp. 4461-4467 (1993).

Ohtsuki, T., et al., "Unnatural base pairs for specific transcription," Proc. Natl. Acad. Sci., vol. 98, No. 9, pp. 4922-4925 (2001).

Hirao, I., et al., "An unnatural base pair for incorporating amino acid analogs into proteins," Nat. Biotech., vol. 20, pp. 177-182 (2002).

Hirao, I., et al., "A Two-Unnatural-Base-Pair System toward the Expansion of the Genetic Code," J. Am. Chem. Soc., vol. 126, pp. 13298-13305 (2004).

Cheetham, G.M.T., et al., "Structural basis for initiation of transcription from an RNA polymerase-promoter complex," Nature, vol. 399, pp. 80-83 (1999).

Yin, Y.W., et al., "The Structural Mechanism of Translocation and Helicase Activity in T7 RNA Polymerase," Cell, vol. 116, pp. 393-404 (2004).

Temiakov, D., et al., "Structural Basis for Substrate Selection by T7 RNA Polymerase," Cell, vol. 116, pp. 389-391 (2004).

Hirao, I., et al., "Unnatural base pairs between 2- and 6-substituted purines and 2-oxo(1H)pyridine for expansion of the genetic alphabet," Bioorg. Med. Chem. Letters, vol. 14, pp. 4887-4890 (2004).

Jovine, L., "The Crystal Structure of Yeast Phenylalanine tRNA at 2.0 A Resolution: Cleavage by $Mg^{2+}$ in 15-year Old Crystals," J. Mol. Biol., vol. 301, pp. 401-414 (2000).

Law, S.M., "Spectroscopic and Calorimetric Characterizations of DNA Duplexes Containing 2-Aminopurine," Biochem., vol. 35, pp. 12329-12337 (1996).

Bain, J.D., et al., "Ribosome-mediated incorporation of a non-standard amino acid into a peptide through expansion of the genetic code," Nature, vol. 356, pp. 537-539 (1992).

Ludwig, J, et al., "Rapid and Efficient Synthesis of Nucleoside 5'-O-(1-Thiotriphosphates), 5'-Triphosphates and 2',3'-Cyclophosphorothioates Using 2-Chloro-4$H$-1,3,2-benzodioxaphosphorin-4-one," J. Org. Chem., Bol 54, pp. 631-635 (1989).

Frugier, M., et al., "Sequences Outside Recognition Sets Are Not Neutral for tRNA Aminoacylation," J. Biol. Chem., vol. 273, No. 19, pp. 11605-11610 (1998).

Mitsui, T., et al., "An Unnatural Hydrophobic Base, 4-Propynylpyrrole-2-carbaldehyde, as an Efficient Pairing Partner of 9-Methylimidazo[(4,5)-$b$]pyridine," Bioorg. Med. Chem. Letters, vol. 13, pp. 4515-4518 (2003).

Fujiwara, T., et al., "Synthesis of 6-(2-Thienyl)purine Nucleoside Derivatives That Form Unnatural Base Pairs with Pyridin-2-one Nucleosides," Bioorg. Med. Chem. Letters, vol. 11, pp. 2221-2223 (2001).

Mitsui, T., et al., "An Efficient Unnatural Base Pair for a Base-Pair-Expanded Transcription System," J. Am. Chem. Soc., vol. 127, pp. 8652-8658 (2005).

Hirao, I., et al., "Efforts toward creating unnatural base pairs for an expanded genetic code," Nucleic Acids Res. Suppl. No. 1, pp. 17-18 (2001).

Mitsui, T., et al., "Enzymatic incorporation of an unnatural base pair between 4-propynyl-pyrrole-2-carbaldehyde and 9-methyl-imidazo[(4,5)-b]pyridine into nucleic acids," Nucleic Acids Res. Suppl. No. 2, pp. 219-220 (2002).

Ichiro Hirao, Dai 28 Kai Annual Meeting of the Molecular of the Molecular Biology Society of Japan Koen Yoshishu, Nov. 25, 2005, p. 62, W2A-2.

Figure 10 a
Template DNA
NonTemp:Bhp2-cont 5'-AGAATTTAATACGACTCACTATAGGGAATCCCGAGTAGTGCTACTAATAAAATGCACTAGTG
Temp:Bhp2-1      3'-TCTTAAATTATGCTGAGTGATATCCCTTAGGGCTCvTCACGATGATTATTTTACGTGAPCAC
                                             +1           +13                          +36 +39

NonTemp:Bhp2-cont 5'-AGAATTTAATACGACTCACTATAGGGAATCCCGAGTAGTGCTACTAATAAAATGCACTAGTG
Temp:Bhp2-2      3'-TCTTAAATTATGCTGAGTGATATCCCTTAGGGCTCATCvCGATGATTATTTTACGPGATCAC
                                             +1              +16                     +33    +39

NonTemp:Bhp2-cont 5'-AGAATTTAATACGACTCACTATAGGGAATCCCGAGTAGTGCTACTAATAAAATGCACTAGTG
Temp:Bhp2-3      3'-TCTTAAATTATGCTGAGTGATATCCCTTAGGGCTCATCACGvTGATTATTTPACGTGATCAC
                                             +1                 +19       +29         +39

P in the sequences represents an artificial base Pa.

T7 RNA polymerase
1 mM natural NTPs,
0-1 mM sTP, and 0-1 mM yTP
[γ-$^{32}$P]GTP, 37°C, 3 h 5'-$^{32}$pppGGGAAUCCCGAGNAGNGCNACUAAUAAANUGCNCUNGUG
    +1              +13 +16 +19          +29 +33 +36 +39 b
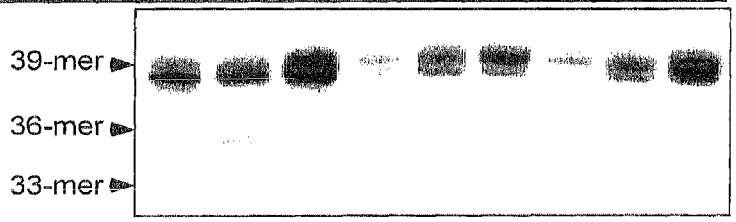

Figure 12 a  Bhp2-1 (39-mer)
5'-GGGAAUCCCGAGyAGUGCUACUAAUAAAAUGCACUsGUG
3'-CCCUUAGGGCUCAUCACGAUGAUUAUUUUACGUGAUCACGGG
complementary RNA (42-mer)

y in the sequences denotes y or FAM-y.

in the absence of complementary RNA in the presence of complementary RNA

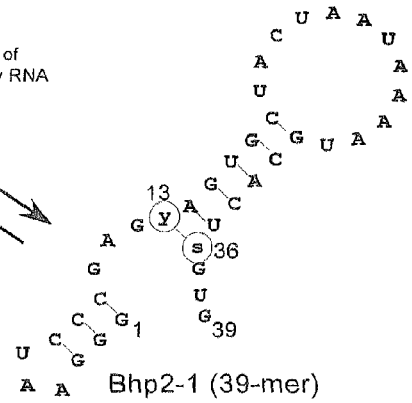

Bhp2-1 (39-mer)

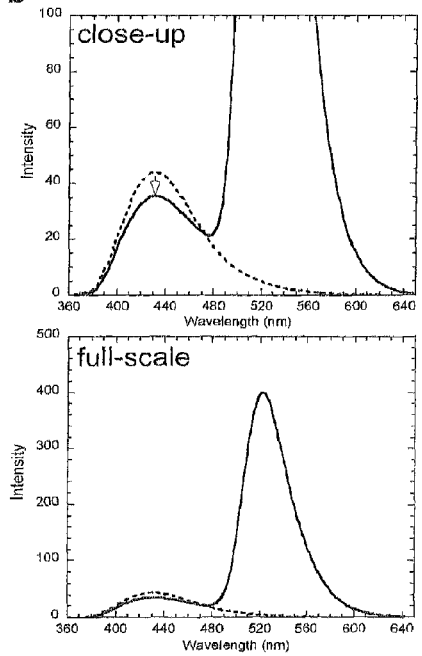

Duplex with complementary RNA

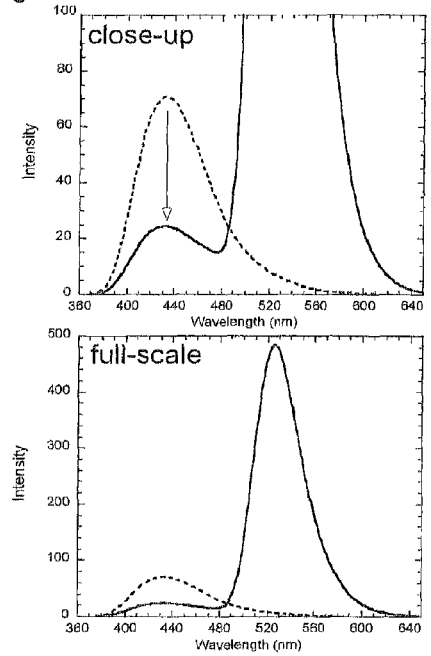

Hairpin

---------- Bhp2-1 having y at position 13 and s at position 36
―――――――― Bhp2-1 having FAM-y at position 13 and s at position 36

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
ataatacgac tcactatagg g                                              21

<210> SEQ ID NO 2
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: 3
<223> OTHER INFORMATION: n means any of the following:
      cytosine, 2-formyl-1H-pyrrol-1-yl, 2-oxo-1,3-dihydroimidazol-1-yl
<220> FEATURE:
<221> NAME/KEY: misc_feature
<222> LOCATION: 4
<223> OTHER INFORMATION: n means any of the following:
      adenine, 2-formyl-1H-pyrrol-1-yl, 2-oxo-1,3-dihydroimidazol-1-yl
<220> FEATURE:
<221> NAME/KEY: misc_feature
<222> LOCATION: 5
<223> OTHER INFORMATION: n means any of the following:
      cytosine, 2-formyl-1H-pyrrol-1-yl, 2-oxo-1,3-dihydroimidazol-1-yl

<400> SEQUENCE: 2
ctnnnaggga agctccctat agtgagtcgt attat                               35
```

```
<210> SEQ ID NO 3
<211> LENGTH: 17
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: 13
<223> OTHER INFORMATION: n means any of the following:
      2-amino-6-(2-thienyl)-purin-9-yl or guanine
<220> FEATURE:
<221> NAME/KEY: misc_feature
<222> LOCATION: 14
<223> OTHER INFORMATION: n means any of the following:
      2-amino-6-(2-thienyl)-purin-9-yl or thymine
<220> FEATURE:
<221> NAME/KEY: misc_feature
<222> LOCATION: 15
<223> OTHER INFORMATION: n means any of the following:
      2-amino-6-(2-thienyl)-purin-9-yl or guanine

<400> SEQUENCE: 3
gggagcuucc cunnnag                                                   17

<210> SEQ ID NO 4
<211> LENGTH: 94
<212> TYPE: DNA
<213> ORGANISM: Artificial
<220> FEATURE:
<223> OTHER INFORMATION: Synthetic

<400> SEQUENCE: 4
ataatacgac tcactatagg ggatttagct cagttgggag agcgccagac tgaagatctg    60
gaggtcctgt gttcgatcca cagaattccc acca                                94

<210> SEQ ID NO 5
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm

<400> SEQUENCE: 5
nngtgggaat tctgtggatc gaacacagga cctccagatc ttcagtctgg cgctctccca    60
actgagctaa atcccctata gtgagtcgta ttat                                94

<210> SEQ ID NO 6
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm
<220> FEATURE:
```

```
<221> NAME/KEY: misc_feature
<222> LOCATION: 61
<223> OTHER INFORMATION: n means 2-formyl-1H-pyrrol-1-yl

<400> SEQUENCE: 6
nngtgggaat tctgtggatc gaacacagga cctccagatc ttcagtctgg cgctctccca      60
nctgagctaa atcccctata gtgagtcgta ttat                                  94

<210> SEQ ID NO 7
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm
<220> FEATURE:
<221> NAME/KEY: misc_feature
<222> LOCATION: 60
<223> OTHER INFORMATION: n means 2-formyl-1H-pyrrol-1-yl

<400> SEQUENCE: 7
nngtgggaat tctgtggatc gaacacagga cctccagatc ttcagtctgg cgctctcccn      60
actgagctaa atcccctata gtgagtcgta ttat                                  94

<210> SEQ ID NO 8
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm
<220> FEATURE:
<221> NAME/KEY: misc_feature
<222> LOCATION: 41
<223> OTHER INFORMATION: n means 2-formyl-1H-pyrrol-1-yl

<400> SEQUENCE: 8
nngtgggaat tctgtggatc gaacacagga cctccagatc ntcagtctgg cgctctccca      60
actgagctaa atcccctata gtgagtcgta ttat                                  94

<210> SEQ ID NO 9
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm
<220> FEATURE:
<221> NAME/KEY: misc_feature
<222> LOCATION: 30
```

<223> OTHER INFORMATION: n means 2-formyl-1H-pyrrol-1-yl

<400> SEQUENCE: 9

```
nngtgggaat tctgtggatc gaacacaggn cctccagatc ttcagtctgg cgctctccca    60
actgagctaa atcccctata gtgagtcgta ttat                                94
```

<210> SEQ ID NO 10
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm
<220> FEATURE:
<221> NAME/KEY: misc_feature
<222> LOCATION: 20
<223> OTHER INFORMATION: n means 2-formyl-1H-pyrrol-1-yl

<400> SEQUENCE: 10

```
nngtgggaat tctgtggatn gaacacagga cctccagatc ttcagtctgg cgctctccca    60
actgagctaa atcccctata gtgagtcgta ttat                                94
```

<210> SEQ ID NO 11
<211> LENGTH: 94
<212> TYPE: DNA
<213> ORGANISM: Artificial
<220> FEATURE:
<223> OTHER INFORMATION: Synthetic
<220> FEATURE:
<221> NAME/KEY: modified_base
<222> LOCATION: 1
<223> OTHER INFORMATION: tm
<220> FEATURE:
<221> NAME/KEY: modified_base
<222> LOCATION: 2
<223> OTHER INFORMATION: gm
<220> FEATURE:
<221> NAME/KEY: misc_feature
<222> LOCATION: 18
<223> OTHER INFORMATION: n means 2-formyl-1H-pyrrol-1-yl

<400> SEQUENCE: 11

```
nngtgggaat tctgtggntc gaacacagga cctccagatc ttcagtctgg cgctctccca    60
actgagctaa atcccctata gtgagtcgta ttat                                94
```

<210> SEQ ID NO 12
<211> LENGTH: 76
<212> TYPE: RNA
<213> ORGANISM: Saccharomyces cerevisiae
<220> FEATURE:
<223> OTHER INFORMATION: tRNA Phe

<400> SEQUENCE: 12

```
ggggauuuag cucaguuggg agagcgccag acugaagauc uggagguccu guguucgauc    60
cacagaauuc ccacca                                                    76
```

<210> SEQ ID NO 13
<211> LENGTH: 62
<212> TYPE: DNA
<213> ORGANISM: Artificial
<220> FEATURE:

<223> OTHER INFORMATION: Synthetic

<400> SEQUENCE: 13
agaatttaat acgactcact atagggaatc ccgagtagtg ctactaataa aatgcactag    60
tg                                                                  62

<210> SEQ ID NO 14
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: 4
<223> OTHER INFORMATION: n means 2-formyl-1H-pyrrol-1-yl
<220> FEATURE:
<221> NAME/KEY: misc_feature
<222> LOCATION: 27
<223> OTHER INFORMATION: n means 2-amino-6-(2-thiazolyl)-purin-9-yl

<400> SEQUENCE: 14
cacnagtgca ttttattagt agcactnctc gggattccct atagtgagtc gtattaaatt    60
ct                                                                  62

<210> SEQ ID NO 15
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: 7
<223> OTHER INFORMATION: n means 2-formyl-1H-pyrrol-1-yl
<220> FEATURE:
<221> NAME/KEY: misc_feature
<222> LOCATION: 24
<223> OTHER INFORMATION: n means 2-amino-6-(2-thiazolyl)-purin-9-yl

<400> SEQUENCE: 14
cactagngca ttttattagt agcnctactc gggattccct atagtgagtc gtattaaatt    60
ct                                                                  62

<210> SEQ ID NO 16
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: 11
<223> OTHER INFORMATION: n means 2-formyl-1H-pyrrol-1-yl
<220> FEATURE:
<221> NAME/KEY: misc_feature
<222> LOCATION: 21
<223> OTHER INFORMATION: n means 2-amino-6-(2-thiazolyl)-purin-9-yl

<400> SEQUENCE: 16
cactagtgca ntttattagt ngcactactc gggattccct atagtgagtc gtattaaatt    60
ct                                                                  62

<210> SEQ ID NO 17
<211> LENGTH: 39
<212> TYPE: RNA
<213> ORGANISM: Artificial
<220> FEATURE:

```
<223> OTHER INFORMATION: Synthetic
<220> FEATURE:
<221> NAME/KEY: misc_feature
<222> LOCATION: 13, 16, 19
<223> OTHER INFORMATION: n means 2-oxo-(1H)pyridin-3-yl or thymine
<220> FEATURE:
<221> NAME/KEY: misc_feature
<222> LOCATION: 29, 33, 36
<223> OTHER INFORMATION: n means 2-amino-6-(2-thienyl)-purin-9-yl or
      adenine

<400> SEQUENCE: 17
gggaaucccg agnagngcna cuaauaaanu gcncungug                            39

<210> SEQ ID NO 18
<211> LENGTH: 39
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: 13
<223> OTHER INFORMATION: n means 2-oxo-(1H)pyridin-3-yl
<220> FEATURE:
<221> NAME/KEY: misc_feature
<222> LOCATION: 36
<223> OTHER INFORMATION: n means 2-amino-6-(2-thienyl)-purin-9-yl

<400> SEQUENCE: 18
gggaaucccg agnagugcua cuaauaaaau gcacungug                            39

<210> SEQ ID NO 19
<211> LENGTH: 42
<212> TYPE: RNA
<213> ORGANISM: Artificial
<220> FEATURE:
<223> OTHER INFORMATION: Synthetic

<400> SEQUENCE: 19
gggcacuagu gcauuuuauu aguagcacua cucgggauuc cc                        42

<210> SEQ ID NO 20
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: 3
<223> OTHER INFORMATION: n means any of the followings:
      cytosine, [2-amino-6-(2-thienyl)purine-9-yl] or
      [2-amino-6-(2-thiazolyl)purine-9-yl]
<220> FEATURE:
<221> NAME/KEY: misc_feature
<222> LOCATION: 4
<223> OTHER INFORMATION: n means any of the followings:
      thymidine, [2-amino-6-(2-thienyl)purine-9-yl] or
      [2-amino-6-(2-thiazolyl)purine-9-yl]
<220> FEATURE:
<221> NAME/KEY: misc_feature
<222> LOCATION: 5
<223> OTHER INFORMATION: n means any of the followings:
      [2-amino-6-(2-thienyl)purine-9-yl] or
      2-amino-6-(2-thiazolyl)purine-9-yl]

<400> SEQUENCE: 20
cannnctcgg gattccctat agtgagtcgt attat                                35

<210> SEQ ID NO 21
<211> LENGTH: 17
```

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: 13
<223> OTHER INFORMATION: n means 2-oxo-(1H)pyridin-3-yl

<400> SEQUENCE: 21
gggaaucccg agnagug                                              17

<210> SEQ ID NO 22
<211> LENGTH: 21
<212> TYPE: DNA
<213> ORGANISM: Artificial
<220> FEATURE:
<223> OTHER INFORMATION: synthetic

<400> SEQUENCE: 22
ataatacgac tcactatagg g                                         21
```

ARTIFICIAL BASE PAIRS AND USES THEREOF

TECHNICAL FIELD

The present application claims priority to Japanese Patent Application Nos. 2005-226492 (filed on Aug. 4, 2005) and 2006-182062 (filed on Jun. 30, 2006), the entire contents of which are incorporated herein by reference.

The present invention relates to nucleic acids based on novel artificial base pairing and uses thereof.

BACKGROUND ART

In nucleic acids (DNA, RNA) which are biological macromolecules, enormous amounts of genetic information essential for vital activities are recorded as sequences composed of combinations of only 4 different bases. Such a nucleic acid allows self-replication using itself as a template by the action of DNA polymerases, and further undergoes processes of RNA polymerase-mediated transcription and ribosome-mediated translation to ensure the transmission of genetic information from DNA to DNA, from DNA to RNA, and/or from RNA to protein. These replication and transmission events of genetic information enabled exclusive base-pairings (A:T/U, G:C). In addition, nucleic acids can form a variety of higher-order structures and hence exert various functions. By way of example, it is one of the indications that a large number of novel nucleic acids having aptamer and/or ribozyme functions have been generated by in vitro selection techniques.

However, unlike proteins which are composed of 20 types of amino acids, the chemical and physical diversity of nucleic acids is limited by the fact that there are only 4 different bases (2 base pairs) in natural nucleic acids. For example, functional RNAs (e.g., tRNA, rRNA, mRNA) found in living organisms utilize various modified bases to stabilize their own structures and/or RNA-RNA and RNA-protein interactions. Thus, it will be very advantageous to expand the repertory of new bases (base pairs) in developing novel functional nucleic acids.

With the aim of further expansion of nucleic acid functions, attempts have been made to design nucleosides or nucleotides having unnatural bases. There are two possible approaches for introducing modified bases (or unnatural bases) into nucleic acids: 1) direct introduction by chemical synthesis; and 2) introduction catalyzed by DNA and RNA polymerase enzymes. In the case of 1), there is a need to solve some problems associated with chemical synthesis, such as the stability of amidite units and the presence of protecting groups appropriate for base moieties. If these problems are solved, various unnatural bases can be introduced in a site-selective manner. However, the nucleic acids thus obtained are difficult to be amplified and it is also difficult to synthesize long-chain nucleic acids. In the case of 2), if the enzymes recognize substrates to cause replication and transcription between artificial base pairs in a complementary manner, nucleic acids containing such artificial base pairs can be amplified and prepared. However, such substrates and base pairs (unnatural nucleotides) are still under development.

Research Background of Unnatural Artificial Base Pairs

In natural double-stranded DNA, the "exclusive" A-T and G-C base pairs are formed through specific hydrogen bonding. Studies of unnatural base pairs have been known for combinations based on hydrogen bonding between bases and/or combinations based on the hydrophobicity of bases, but no unnatural base pair has been found that can compete with natural base pairs in all steps of replication, transcription and translation. Under these circumstances, an unnatural base pair capable of competing with natural base pairs in at least one step of replication, transcription and translation will have a specific utility.

Recent studies of unnatural non-hydrogen-bonded base pairs have shown that hydrogen bonding between paired bases is not absolutely required for efficient and adequate incorporation of nucleotides during replication; rather, shape complementarity between bases plays an important role during replication (Non-patent Documents 5-6). Thus, non-hydrogen-bonded base pairs are potential candidates for expansion of the genetic alphabet and code to create novel biotechnologies (Non-patent Documents 7-9).

On the other hand, no report has been issued on a non-hydrogen-bonded base pair that is recognized by RNA polymerase with high selectivity and efficiency during transcription. More specifically, the inventors of the present invention have developed a (s-y) base pair through interaction of hydrogen bonding between a 2-amino-6-(2-thienyl)-9H-purin-9-yl group (s) and a 2-oxo-(1H)pyridin-3-yl group (y), and have succeeded in in vitro synthesis of proteins site-specifically containing an unnatural amino acid(s) (Patent Document 1, Non-patent Document 14).

Moreover, Patent Document 3 discloses a (v-y) base pair between a 2-amino-6-(2-thiazolyl)purin-9-yl group (v) and a 2-oxo-(1H)pyridin-3-yl group (y) (Patent Document 3).

As the nucleic acid base pairs of s, (s-z) (wherein z represents a 2-oxo-1,3-dihydroimidazol-1-yl group) and (s-5-substituted y) other than the four natural bases and (s-y) has been reported prior to the present invention. These unnatural (s-y), (s-z) and (s-5-substituted y) base pairs all involve hydrogen bonding interaction (Patent Document 2, Non-patent Documents 13-15).

However, among these unnatural base pairs, (s-y) and (s-5-substituted y) are less selective in a transcription step where s is inserted into RNA using y as a DNA template, while (s-z) is highly selective, but does not necessarily provide high yield.

[Formula 1]

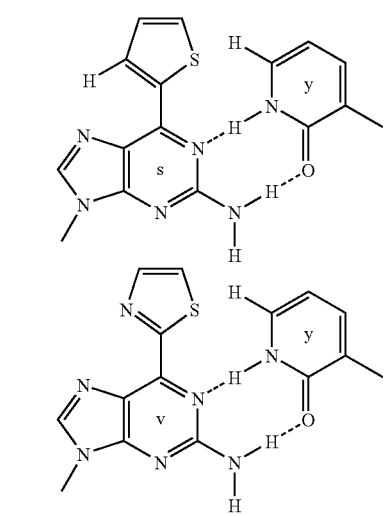

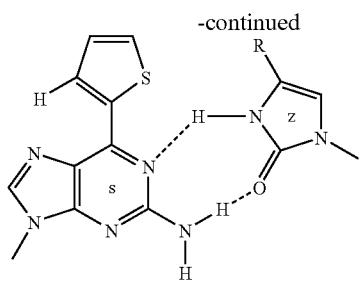

On the other hand, a 2-formyl-1H-pyrrol-1-yl group (Pa) has been reported to be able to form non-hydrogen-bonded base pairs not only with the four natural bases, but also with 9-methylimidazo[(4,5)-b]pyridine (Q) (Pa-Q) (Non-patent Document 9).

[Formula 2]

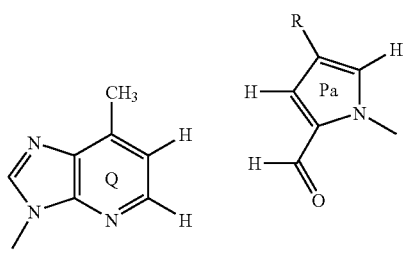

However, the above non-hydrogen-bonded base pairs are reported only for translation by DNA polymerase or DNA synthesis by reverse transcriptase. There is no knowledge about their recognition by RNA polymerase. A single subunit of T7-like RNA polymerase resembles DNA polymerase both in structure and mechanism (Non-patent Documents 16-17), but recent structural analyses of T7 RNA polymerase complexes have clarified differences between RNA polymerase and DNA polymerase (Non-patent Documents 17-18). In the case of transcription, an incoming substrate forms a base pair with a base in its template in the "open" conformation, and the formed base pair is maintained during transition from "open" to "closed" conformation (Non-patent Document 18). However, in the case of replication, base pairing starts after transition to the "closed" conformation. This suggests that hydrogen bonding between paired bases is more important in transcription than in replication, which in turn leads to a question of whether non-hydrogen-bonded base pairs could be functional during transcription.

If unnatural base-mediated specific transcription is achieved, it will be possible to design novel RNA molecules having promoted functions and to expand the genetic code (Non-patent Documents 1-4).

Introduction of Fluorescent Probes into RNA

In response to recent growing interest in RNA therapy, introduction of fluorescent probes into RNA have become an important technology for fluorescently labeling RNA and for analyzing the complex higher order structure of RNA. Fluorescent probes previously used for the latter structural analysis include those using a nucleotide having a fluorescent base (e.g., 2-aminopurine). In this regard, the 2-amino-6-(2-thienyl)-9H-purin-9-yl group (s) mentioned above is a fluorescent base, and a nucleotide containing this group as a base has strong fluorescence properties. Thus, if a nucleotide containing s as a base can be introduced at any site in RNA, it will be possible to prepare a useful fluorescent probe.

However, known techniques used for introducing such a nucleotide having a fluorescent base into RNA through transcription are not necessarily sufficient in terms of yield. It has therefore been substantially impossible to introduce a nucleotide having a fluorescent base (e.g., s) into RNA in a site-specific manner through transcription, thus making it difficult to analyze a higher order structure of long-chain RNA.

Once a technique has been developed for introducing a fluorescent probe into RNA through transcription, it will be possible to study structural dynamics of RNA in a solution. Moreover, such a technique would be also helpful in developing RNA-based drugs. For these reasons, it is important to establish a technique that allows introduction of a fluorescent probe into long-chain RNA, which has thus far been regarded as impossible. This would enable the development of new techniques for use in in vivo structural analysis of functional RNA and in structural analysis of RNA complexes with other molecules.

There is a demand for the development of a novel artificial base pair for use in introducing, into a nucleic acid, a nucleotide having an unnatural base which can compete with natural base pairs in all steps of replication, transcription and translation and which imparts fluorescence properties to a nucleic acid.

Patent Document 1: WO2001/005801
Patent Document 2: WO2004/007713
Patent Document 3: WO2005/026187
Non-patent Document 1: Benner, S. A., Burgstaller, P., Battersby, T. R. & Jurczyk, S. in The RNA World (eds Gesteland, R. F., Cech, T. R. & Atkins, J. F.) 163-181 (Cold Spring Harbor Laboratory Press, Cold Spring Harbor, N.Y., 1999).
Non-patent Document 2: Bergstrom, D. E. Orthogonal base pairs continue to evolve. Chem. Biol. 11, 18-20 (2004).
Non-patent Document 3: Wang, L. & Schultz, P. G. Expanding the genetic code. Chem. Commun. 1-11 (2002).
Non-patent Document 4: Hendrickson, T. L., de Crecy-Lagard, V. & Schimmel, P. Incorporation of nonnatural amino acids into proteins. Annu. Rev. Biochem. 73, 147-176 (2004).
Non-patent Document 5: Morales, J. C. & Kool, E. T. Efficient replication between non-hydrogen-bonded nucleoside shape analogs. Nat. Struct. Biol. 5, 950-954 (1998).
Non-patent Document 6: Kool, E. T. Hydrogen bonding, base stacking, and steric effects in DNA replication. Annu. Rev. Biophys. Biomol. Struct. 30, 1-22 (2001).
Non-patent Document 7: McMinn, D. L. et al. Efforts toward expansion of the genetic alphabet: DNA polymerase recognition of a highly stable, self-pairing hydrophobic base. J. Am. Chem. Soc. 121, 11585-11586 (1999).
Non-patent Document 8: Wu, Y. et al. Efforts toward expansion of the genetic alphabet: optimization of interbase hydrophobic interactions. J. Am. Chem. Soc. 122, 7621-7632 (2000).
Non-patent Document 9: Mitsui, T. et al. An unnatural hydrophobic base pair with shape complementarity between pyrrole-2-carbaldehyde and 9-methylimidazo[(4,5)-b]pyridine. J. Am. Chem. Soc. 125, 5298-5307 (2003).
Non-patent Document 10: Piccirilli, J. A., Krauch, T., Moroney, S. E. & Benner, S. A. Enzymatic incorporation of a new base pair into DNA and RNA extends the genetic alphabet. Nature 343, 33-37 (1990).
Non-patent Document 11: Switzer, C. Y., Moroney, S. E. & Benner, S. A. Enzymatic recognition of the base pair between isocytidine and isoguanosine. Biochemistry 32, 10489-10496 (1993).

Non-patent Document 12: Tor, Y. & Dervan, P. B. Site-specific enzymatic incorporation of an unnatural base, N[6]-(6-aminohexyl)isoguanosine, into RNA. J. Am. Chem. Soc. 115, 4461-4467 (1993).

Non-patent Document 13: Ohtsuki, T. et al. Unnatural base pairs for specific transcription. Proc. Natl. Acad. Sci. U.S.A. 98, 4922-4925 (2001).

Non-patent Document 14: Hirao, I. et al. An unnatural base pair for incorporating amino acid analogs into proteins. Nat. Biotechnol. 20, 177-182 (2002).

Non-patent Document 15: Hirao, I. et al. A two-unnatural-base-pair system toward the expansion of the genetic code. J. Am. Chem. Soc. 126, 113298-113305 (2004).

Non-patent Document 16: Cheetham, G. M., Jeruzalmi, D. & Steitz, T. A. Structural basis for initiation of transcription from an RNA polymerase-promoter complex. Nature 399, 80-83 (1999).

Non-patent Document 17: Yin, Y. W. & Steitz, T. A. The structural mechanism of translocation and helicase activity in T7 RNA polymerase. Cell 116, 393-404 (2004).

Non-patent Document 18: Temiakov, D. et al. Structural basis for substrate selection by T7 RNA polymerase. Cell 116, 381-391 (2004).

Non-patent Document 19: Hirao, I., Fujiwara, T., Kimoto, M. & Yokoyama, S. Unnatural base pairs between 2- and 6-substituted purines and 2-oxo(1H)pyridine for expansion of the genetic alphabet. Bioorg. Med. Chem. Lett. 14, 4887-4890 (2004).

Non-patent Document 20: Jovine, L., Djordjevic, S. & Rhodes, D. The crystal structure of yeast phenylalanine tRNA at 2.0 Å resolution: cleavage by $Mg^{2+}$ in 15-year old crystals. J. Mol. Biol. 301, 401-414 (2000).

Non-patent Document 21: Law, S. M., Eritja, R., Goodman, M. F. & Breslauer, K. J. Spectroscopic and calorimetric characterizations of DNA duplexes containing 2-aminopurine. Biochemistry 35, 12329-12337 (1996).

Non-patent Document 22: Holz, B., Klimasauskas, S., Serva, S. & Weinhold, E. 2-Aminopurine as a fluorescent probe for DNA base flipping by methyltransferases. Nucleic Acids Res. 26, 1076-1083 (1998).

Non-patent Document 23: Rist, M. J. & Marino, J. P. Association of an RNA kissing complex analyzed using 2-aminopurine fluorescence. Nucleic Acids Res. 29, 2401-2408 (2001).

Non-patent Document 24: Bain, J. D., Switzer, C., Chamberlin, A. R. & Benner, S. A. Ribosome-mediated incorporation of a non-standard amino acid into a peptide through expansion of the genetic code. Nature 356, 537-539 (1992).

Non-patent Document 25: Ludwig, J. & Eckstein, F. Rapid and efficient synthesis of nucleoside 5'-O-(1-thiotriphosphates), 5'-triphosphates and 2',3'-cyclophosphorothioates using 2-chloro-4H-1,3,2-benzodioxaphosphorin-4-one. J. Org. Chem. 54, 631-635 (1989).

Non-patent Document 26: Frugier, M., Helm, M., Felden, B., Giege, R. & Florentz, C. Sequences outside recognition sets are not neutral for tRNA aminoacylation. J. Biol. Chem. 273, 11605-11610 (1998).

Non-patent Document 27: Kao, C., Rudisser, S. & Zheng, M. A simple and efficient method to transcribe RNAs with reduced 3' heterogeneity. Methods 23, 201-205 (2001).

Non-patent Document 28: Mitsui, T., Kimoto, M., Sato, A., Yokoyama, S. & Hirao, I., Bioorg. Med. Chem. Lett., 13, 4515-4518 (2003)

Non-patent Document 29: Fujiwara, T., Kimoto, M., Sugiyama, H., Hirao, I. & Yokoyama, S., Bioorg. Med. Chem. Lett., 11, 2221-2223 (2001)

Non-patent Document 30: Mitsui, T., Kimoto, M., Harada, Y., Yokoyama, S. & Hirao, I., J. Am. Chem. Soc., 127, 8652-8658 (2005)

DISCLOSURE OF THE INVENTION

Problems to be Solved by the Invention

The present invention aims to provide a nucleic acid based on novel artificial base pairing. More specifically, in the nucleic acid of the present invention, a nucleotide having a substituted or unsubstituted 2-formyl-1H-pyrrol-1-yl group as a base forms a base pair with a nucleotide having a 6-substituted 9H-purin-9-yl group as a base.

Without being limited thereto, in the nucleic acid of the present invention, the above substituted or unsubstituted 2-formyl-1H-pyrrol-1-yl group is preferably selected from the group consisting of:
A1) a 2-formyl-1H-pyrrol-1-yl group;
A2) a 2-formyl-4-(1-propyn-1-yl)-1H-pyrrol-1-yl group;
A3) a 2-formyl-4-methyl-1H-pyrrol-1-yl group; and
A4) a 2-formyl-4-ethynyl-1H-pyrrol-1-yl group,
and the above 6-substituted 9H-purin-9-yl group is preferably selected from the group consisting of:
B1) a 2-amino-6-(2-thienyl)-9H-purin-9-yl group;
B2) a 6-(2-thienyl)-9H-purin-9-yl group;
B3) a 2-amino-6-(4-methyl-2-thienyl)-9H-purin-9-yl group;
B4) a 6-(4-methyl-2-thienyl)-9H-purin-9-yl group;
B5) a 2-amino-6-(5-methyl-2-thienyl)-9H-purin-9-yl group;
B6) a 6-(5-methyl-2-thienyl)-9H-purin-9-yl group;
B7) a 2-amino-6-(2-thiazolyl)-9H-purin-9-yl group;
B8) a 6-(2-thiazolyl)-9H-purin-9-yl group;
B9) a 2-amino-6-(4-methyl-2-thiazolyl)-9H-purin-9-yl group;
B10) a 6-(4-methyl-2-thiazolyl)-9H-purin-9-yl group;
B11) a 2-amino-6-(5-methyl-2-thiazolyl)-9H-purin-9-yl group; and
B12) a 6-(5-methyl-2-thiazolyl)-9H-purin-9-yl group.

The nucleic acid of the present invention preferably forms a base pair(s) in the step of transcription, reverse transcription, replication or translation.

The present invention also provides a method for preparing a nucleic acid incorporating a nucleotide having a 6-substituted 9H-purin-9-yl group as a base. The preparation method of the present invention comprises effecting transcription, reverse transcription or replication by using, as a template, a nucleic acid incorporating a nucleotide having a substituted or unsubstituted 2-formyl-1H-pyrrol-1-yl group as a base, so that the nucleotide having a 6-substituted 9H-purin-9-yl group is incorporated at a site complementary to the nucleotide having a substituted or unsubstituted 2-formyl-1H-pyrrol-1-yl group.

The present invention further aims to provide such a nucleic acid incorporating a nucleotide having a 6-substituted 9H-purin-9-yl group as a base, which is prepared by the above method of the present invention.

The present invention further aims to provide a method for analyzing the stereostructure of a local region in the nucleic acid of the present invention, wherein the local region includes a nucleotide having a 6-substituted 9H-purin-9-yl group as a base. The analysis method of the present invention comprises measuring the fluorescence intensity from the base in the nucleotide having a 6-substituted 9H-purin-9-yl group as a base, under different environmental conditions such as varying temperatures or ion (e.g., magnesium) concentrations.

In one embodiment of the analysis method of the present invention, a determination is made that the nucleotide having a 6-substituted 9H-purin-9-yl group as a base stacks with its conformationally neighboring nucleotides at in vivo temperature if the fluorescence intensity from the base in the nucleotide is substantially increased with increase in temperature, or alternatively, a determination is made that the nucleotide is exposed outside at in vivo temperature if the fluorescence intensity is substantially decreased or not increased with increase in temperature.

The present invention also aims to provide a method for detecting the formation of a nucleic acid duplex. The detection method of the present invention comprises:

I) inducing hybridization between the following nucleic acids:

i) a nucleic acid incorporating a nucleotide having a 6-substituted 9H-purin-9-yl group as a base, which is prepared by the inventive method for preparing a nucleic acid, and ii) a nucleic acid incorporating a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX); and II) measuring a change in the fluorescence spectrum.

The present invention further aims to provide a method for preparing a nucleic acid incorporating the following nucleotides on the same strand:

i) a nucleotide having a 6-substituted 9H-purin-9-yl group as a base; and ii) a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX). The preparation method of the present invention comprises effecting transcription, reverse transcription or replication by using, as a template, a nucleic acid incorporating the following nucleotides:

iii) a nucleotide having a substituted or unsubstituted 2-formyl-1H-pyrrol-1-yl group as a base; and iv) a nucleotide having a 6-substituted 9H-purin-9-yl group as a base, so that the nucleotide of i) is incorporated at a site complementary to the nucleotide of iii), while the nucleotide of ii) is incorporated at a site complementary to the nucleotide of iv).

The present invention further provides such a nucleic acid prepared by the above method.

The present invention also provides a method for detecting a stem-loop (hairpin) structure formation of the nucleic acid of the present invention incorporating, on the same strand, a nucleotide having a 6-substituted 9H-purin-9-yl group as a base and a nucleotide having a 5-substituted-2-oxo(1H)pyridin-3-yl group as a base. The detection method of the present invention comprises:

1) inducing hybridization between the nucleotide of i) and the nucleotide of ii) in the nucleic acid of the present invention; and 2) measuring a change in the fluorescence spectrum.

Means for Solving the Problems

To solve the problems stated above, the inventors of the present invention have studied base pairs constructed by combining several unnatural bases which had been developed by themselves. As a result, the inventors have found that a combination between 2-amino-6-(2-thienyl)purin-9-yl (s) (Non-patent Documents 13 and 14) and 2-formyl-1H-pyrrol-1-yl (Pa) (Non-patent Document 9) (FIG. 1A) is highly selective and efficient during transcription. Namely, the inventors have found that when this Pa nucleotide is inserted into a DNA template and used for RNA transcription reaction, s is selectively introduced in high yield into the generated RNA at a site complementary to Pa in the template DNA. The inventors have thereby arrived at the present invention.

By the action of T7 RNA polymerase, the substrate s can be inserted in a site-specific manner into RNA generated from a DNA template at a site complementary to Pa in the template. The purine base s has substituents allowing hydrogen bonding (i.e., a hydrogen acceptor at the 1-position and a hydrogen donor amino group at the 2-position). However, Pa does not have such a hydrophilic group on the pairing surface. The inventors of the present invention have found that oxygen in the formyl group of the Pa base does not serve as a hydrogen acceptor during base pairing because it is directed toward the minor groove of double-stranded DNA and interacts with polymerase (Non-patent Document 9). In the present invention, the s-Pa pair has no significant hydrogen bonding interaction, but Pa would have shape complementarity with s because it is a 5-membered ring base.

Nucleic Acids of the Present Invention Based on Artificial Base Pairing

Thus, in one embodiment, the present invention provides a nucleic acid in which a nucleotide having a substituted or unsubstituted 2-formyl-1H-pyrrol-1-yl group as a base forms a base pair with a nucleotide having a 6-substituted 9H-purin-9-yl group as a base.

As used herein, the term "nucleoside" is intended to mean a glycoside compound formed through glycosidic linking between a nucleic acid base and a reducing group of a sugar. It should be noted that the term "nucleic acid base" is intended to encompass adenine, guanine, cytosine, thymine, uracil, and also derivatives thereof. The type of "derivative" is not limited in any way. Specific examples include bases equivalent to a substituted or unsubstituted 2-formyl-1H-pyrrol-1-yl group and bases equivalent to a 6-substituted 9H-purin-9-yl group. The term "nucleotide" refers to a compound in which the sugar moiety of the above nucleoside forms an ester with phosphoric acid, more preferably a mono-, di- or tri-phosphate ester. The sugar moiety of such a nucleoside or nucleotide may be ribofuranosyl, 2'-deoxyribofuranosyl, or 2'-substituted ribofuranosyl having a substituent (e.g., halogen) at the 2'-position. Likewise, the phosphoric acid moiety may be thiophosphoric acid. Namely, the sugar and phosphoric acid moieties may be in the same form as found in known nucleosides, nucleotides, or derivatives thereof. A ribonucleotide whose sugar moiety is ribofuranosyl can be used as a component of RNA, while a deoxyribonucleotide whose sugar moiety is deoxyribofuranosyl can be used as a component of DNA.

The "substituted or unsubstituted 2-formyl-1H-pyrrol-1-yl group" of the present invention has a structure represented by the following general formula:

[Formula 3]

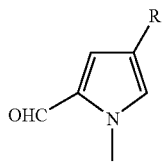

wherein R at the 4-position of the pyrrole ring is hydrogen or may be substituted with a substituent selected from a substituted or unsubstituted $C_1$-$C_3$ alkyl group, a substituted or unsubstituted $C_2$-$C_3$ alkenyl group, or a substituted or unsubstituted $C_2$-$C_8$ alkynyl group. Such an alkyl, alkenyl or alkynyl group may further be substituted with one or more groups independently selected from the group consisting of a lower alkyl group, a halogen group, a hydroxyl group, an amino group, an alkylamino group and an aromatic heterocyclic ring. The substituted or unsubstituted 2-formyl-1H-pyrrol-1-yl group of the present invention is herein referred to as "Pa" or "Pa analog," depending on the context.

Without being limited thereto, the substituted or unsubstituted 2-formyl-1H-pyrrol-1-yl group mentioned above may be selected from the group consisting of:
A1) a 2-formyl-1H-pyrrol-1-yl group (Pa);
A2) a 2-formyl-4-(1-propyn-1-yl)-1H-pyrrol-1-yl group;
A3) a 2-formyl-4-methyl-1H-pyrrol-1-yl group; and
A4) a 2-formyl-4-ethynyl-1H-pyrrol-1-yl group. More preferred is a 2-formyl-1H-pyrrol-1-yl group.

A nucleoside or nucleotide having the "substituted or unsubstituted 2-formyl-1H-pyrrol-1-yl group" ("Pa" or "Pa analog") of the present invention may be synthesized in a known manner. Starting materials (e.g., pyrrole-2-carboxaldehyde) can be purchased from, for example, Aldrich [1003-29-8] or Merck [807574]. Likewise, Pa derivatives may be synthesized by being derived from Pa, in principle. For example, a derivative having propyne introduced at the 4-position of Pa can be found in Bioorg. Med. Chem. Lett., 13, p. 4515-4518 (2003) (Non-patent Document 28).

The "6-substituted 9H-purin-9-yl group" of the present invention has a structure represented by the following general formula:

[Formula 4]

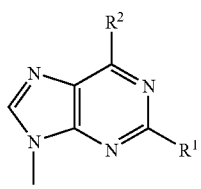

[wherein
$R^1$ is hydrogen or an amino group, and
$R^2$ is a substituted or unsubstituted 2-thienyl or 2-thiazolyl group].

The thienyl or thiazolyl group listed as $R^2$ may be unsubstituted or may be substituted at the 4- and/or 5-position(s) with one or more groups independently selected from the group consisting of a methyl group, an amino group, a nitro group and a hydroxy group. Among members of the 6-substituted 9H-purin-9-yl group of the present invention, those in which $R^2$ is a substituted or unsubstituted 2-thienyl group are herein referred to as "s" or "s analog," depending on the context. Among members of the 6-substituted 9H-purin-9-yl group of the present invention, those in which $R^2$ is a substituted or unsubstituted 2-thiazolyl group are herein referred to as "v" or "v analog," depending on the context.

Without being limited thereto, the 6-substituted 9H-purin-9-yl group mentioned above may be selected from the group consisting of:
B1) a 2-amino-6-(2-thienyl)-9H-purin-9-yl group (s);
B2) a 6-(2-thienyl)-9H-purin-9-yl group (s');
B3) a 2-amino-6-(4-methyl-2-thienyl)-9H-purin-9-yl group;
B4) a 6-(4-methyl-2-thienyl)-9H-purin-9-yl group;
B5) a 2-amino-6-(5-methyl-2-thienyl)-9H-purin-9-yl group;
B6) a 6-(5-methyl-2-thienyl)-9H-purin-9-yl group;
B7) a 2-amino-6-(2-thiazolyl)-9H-purin-9-yl group (v);
B8) a 6-(2-thiazolyl)-9H-purin-9-yl group;
B9) a 2-amino-6-(4-methyl-2-thiazolyl)-9H-purin-9-yl group;
B10) a 6-(4-methyl-2-thiazolyl)-9H-purin-9-yl group;
B11) a 2-amino-6-(5-methyl-2-thiazolyl)-9H-purin-9-yl group; and
B12) a 6-(5-methyl-2-thiazolyl)-9H-purin-9-yl group. More preferred is a 2-amino-6-(2-thienyl)-9H-purin-9-yl group.

Among the above bases, B1) is "s" and B2) to B6) are "s analogs." Likewise, B7) is "v" and B8) to B12) are "v analogs."

In an even more preferred embodiment, the above substituted or unsubstituted 2-formyl-1H-pyrrol-1-yl group is a 2-formyl-1H-pyrrol-1-yl group, and the above 6-substituted 9H-purin-9-yl group is a 2-amino-6-(2-thienyl)-9H-purin-9-yl group.

The "6-substituted 9H-purin-9-yl group" of the present invention and a nucleoside or nucleotide containing the same may be synthesized in a known manner. More specifically, Example 1 described later discloses procedures for synthesis of 2-amino-6-(2-thienyl)-9-(1-β-D-ribofuranosyl)purine 5'-triphosphate (sTP) from 2-N-phenoxyacetyl-6-(2-thienyl)-9-(2,3-di-O-acetyl-1-β-D-ribofuranosyl)purine, by way of example.

Synthesis of s can be found, for example, in the second paragraph on the second page of Bioorg. Med. Chem. Lett., 11, p. 2221-2223 (2001) (Non-patent Document 29). Likewise, synthesis of v is disclosed, for example, in Paragraphs 0026-0027 and FIGS. 5-6 of Patent Document 3, or alternatively, in the right paragraph on the second page of J. Am. Chem. Soc., 127, p. 8652-8658 (2005) (Non-patent Document 30).

In addition to s or v, nucleosides or nucleotides having other members of the "6-substituted 9H-purin-9-yl group" of the present invention may be synthesized in the same manner as used for synthesis of s or v. For example, o having furan attached thereto may also be synthesized in the same manner as used for synthesis of s (Non-patent Document 29).

The present invention provides a nucleic acid in which a nucleotide having a substituted or unsubstituted 2-formyl-1H-pyrrol-1-yl group as a base forms a base pair with a nucleotide having a 6-substituted 9H-purin-9-yl group as a base. As used herein, the term "nucleic acid" is intended to mean a molecule of a nucleic acid strand in which more than one nucleotide is linked in the direction of 5'→3'. The nucleic acid of the present invention encompasses single-stranded or double-stranded RNA or DNA. The double-stranded nucleic acid may be DNA/DNA, RNA/RNA, or DNA/RNA. DNA also includes cDNA obtained by reverse transcription using RNA as a template. Alternatively, the nucleic acid may form a triplex, a quadruplex, etc.

With the aim of further expansion of nucleic acid functions, the inventors of the present invention have attempted to design nucleosides or nucleotides having unnatural bases. Embodiments of newly developed artificial base pairs include a base pair between a nucleotide having a substituted or unsubstituted 2-formyl-1H-pyrrol-1-yl group as a base (e.g., Pa) and a nucleotide having a 6-substituted 9H-purin-9-yl group as a base (e.g., s) (FIG. 1). This enables in particular the specific incorporation of s into RNA during T7 RNA polymerase-mediated transcription using a DNA template containing Pa.

Although there is no significant hydrogen bonding interaction between s and Pa (non-hydrogen-bonded s-Pa pair), the efficiency and selectivity of s-Pa pairing during transcription is as high as that of natural base pairing. This s-Pa pair shows a higher efficiency than the previously developed hydrophilic s-z pair. The complementary shapes of s and Pa are fitted to each other, but their shapes differ from those of natural purines and pyrimidines. This specific stereochemical fitting would eliminate non-canonical pairing with natural bases, thereby resulting in high selectivity between s and Pa during transcription. In this way, shape complementarity plays an important role in specific base pairing during transcription and replication.

In the present invention, a nucleotide having a substituted or unsubstituted 2-formyl-1H-pyrrol-1-yl group as a base and a nucleotide having a 6-substituted 9H-purin-9-yl group as a base are present in two separate nucleic acid strands and can form a duplex through base pairing. Alternatively, these nucleotides may be present in the same single-stranded nucleic acid. In this case, such a single strand may form a loop structure through base pairing.

The nucleotide of the present invention which has a substituted or unsubstituted 2-formyl-1H-pyrrol-1-yl group or a 6-substituted 9H-purin-9-yl group as a base can be incorporated into nucleic acids such as DNA or RNA through transcription, replication or reverse transcription reaction. Alternatively, the nucleotide of the present invention may be incorporated into DNA or RNA through chemical synthesis, as in the case of nucleosides or nucleotides having natural bases.

These transcription, replication and reverse transcription reactions may be accomplished according to known techniques. Without being limited thereto, for example, it is possible to use T7 RNA polymerase (Takara or other suppliers) for transcription, Klenow fragment (KF) for replication, and AMV Reverse Transcriptase XL (AMV-RT, Life Science) for reverse transcription. In order to avoid removal of the nucleotide of the present invention during the reaction, the replication may also be accomplished, for example, by using Taq DNA polymerase (Takara Taq™) lacking 3'→5' exonuclease activity to effect PCR amplification of template DNA with a primer containing a nucleotide having a substituted or unsubstituted 2-formyl-1H-pyrrol-1-yl group as a base.

Without being limited thereto, in one embodiment, the nucleic acid of the present invention forms a base pair(s) in the step of transcription, reverse transcription, replication or translation of the nucleic acid. In a case where the nucleic acid of the present invention forms a base pair(s) in the transcription step, the above nucleotide having a substituted or unsubstituted 2-formyl-1H-pyrrol-1-yl group as a base may be a part of DNA, while the above nucleotide having a 6-substituted 9H-purin-9-yl group as a base may be a part of RNA.

Method for Preparing a Nucleic Acid

The present invention also aims to provide a method for preparing a nucleic acid incorporating a nucleotide having a 6-substituted 9H-purin-9-yl group as a base. The preparation method of the present invention comprises effecting transcription, reverse transcription or replication by using, as a template, a nucleic acid incorporating a nucleotide having a substituted or unsubstituted 2-formyl-1H-pyrrol-1-yl group as a base, so that the nucleotide having a 6-substituted 9H-purin-9-yl group is incorporated at a site complementary to the nucleotide having a substituted or unsubstituted 2-formyl-1H-pyrrol-1-yl group.

The nucleotide having a 2-formyl-1H-pyrrol-1-yl group and the nucleotide having a 6-substituted 9H-purin-9-yl group are as defined herein above in the section "Nucleic acids of the present invention based on artificial base pairing."

As shown in Examples 1 and 2 described later, even in a case where two or more nucleotides having a substituted or unsubstituted 2-formyl-1H-pyrrol-1-yl group as a base are located adjacent to each other in a template, transcription reaction can proceed, so that a nucleotide having a 6-substituted 9H-purin-9-yl group as a base is incorporated at a complementary site. Thus, the method of the present invention enables the preparation of conventionally unavailable DNA and RNA in which two or more unnatural s bases are located adjacent to each other. Thus, in one embodiment of the preparation method of the present invention, the template has two or more nucleotides having a substituted or unsubstituted 2-formyl-1H-pyrrol-1-yl group as a base.

The present invention further aims to provide such a nucleic acid incorporating a nucleotide having a 6-substituted 9H-purin-9-yl group as a base, which is prepared by the above method of the present invention.

The nucleic acid incorporating the nucleotide(s) of the present invention may be used as tRNA, mRNA, antisense DNA or RNA, a ribozyme or an aptamer. The term "antisense DNA or RNA" refers to DNA or RNA capable of inhibiting the expression of a specific gene. It was named to mean that such DNA or RNA is complementary to the full-length or partial sequence of a target gene sequence (sense strand). Antisense DNA or RNA may be used as a tool for artificial regulation of gene expression. Because of containing unnatural bases, such antisense DNA or RNA incorporating the nucleotide(s) of the present invention can be designed to have a different complementarity to a target when compared to the case of using natural bases only. The term "ribozyme" is a generic name for catalysts composed of RNA. The term "aptamer" refers to an in vitro-selected nucleic acid having the ability to bind to a specific molecule such as a protein.

The nucleic acid (DNA or RNA) (e.g., mRNA, synthetic RNA) incorporating the nucleotide(s) of the present invention may also encode all or part of a protein or peptide. The nucleic acid of the present invention may be used, e.g., as a gene fragment or a probe. The present invention also encompasses the following embodiments: partial or complete replacement of native genes by the nucleic acids of the present invention; addition of one or more nucleotides of the present invention to native genes; or combinations thereof.

Furthermore, the nucleic acids of the present invention incorporating nucleotides having unnatural bases may also be used in RNA interference (RNAi). RNA interference is a phenomenon in which double-stranded RNA (dsRNA) induces mRNA degradation in a sequence-specific manner and hence inhibits gene expression. In a typical example of RNA interference, dsRNA is processed by Dicer belonging to the RNaseIII family into siRNA (short interfering RNA) of approximately 21 to 23 bases in length, which has a 3'-terminal overhang of approximately 2 bases. siRNA is associated into an siRNA-protein complex called RISC and induces mRNA degradation in a sequence-specific manner. RNA interference is shown to be a phenomenon conserved among a wide range of organism species including mammals (e.g., human, mouse), nematodes, plants, drosophila and fungi. The nucleic acids of the present invention incorporating nucleotides having unnatural bases can be used as siRNA in RNA interference or as a part of mRNA to be degraded.

Moreover, it is also possible to design a new codon containing the nucleotide of the present invention. As described above, even in a case where two or more nucleotides having a substituted or unsubstituted 2-formyl-1H-pyrrol-1-yl group as a base (e.g., Pa) are located adjacent to each other in a template, transcription reaction can proceed, so that a nucleotide having a 6-substituted 9H-purin-9-yl group as a base (e.g., s) is incorporated at a complementary site. Thus, the method of the present invention enables the preparation of conventionally unavailable DNA and RNA in which two or more unnatural s bases are located adjacent to each other. In turn, it is also possible to design a codon containing three s (sss), those containing two s (e.g., ssA, Gss, sGs) and those containing one s (e.g., sAG, CsT, AGs). Such a new codon may encode either a natural amino acid or an unnatural amino acid. In this way, the present invention not only provides novel unnatural artificial bases, but also enables the design of entirely new genetic codes by designing new codons containing the nucleotides of the present invention, thus providing a world of new genetic codes.

Further, by designing tRNA systems corresponding to the new codons of the present invention, it is also possible to design a new protein synthesis system in which numerous amino acids can be used. Amino acids which can be used are not limited in any way as long as they can be used in the protein-synthesizing enzyme system in ribosomes. Thus, the present invention provides a new protein synthesis system using the above codons of the present invention. According to the protein synthesis system of the present invention, when a nucleic acid corresponding to a codon at a desired site is efficiently replaced by the nucleic acid of the present invention or when the nucleic acid of the present invention is introduced at a desired site in a codon, it is possible to produce a protein containing a desired unnatural amino acid(s).

Method for Analyzing Stereostructure

A nucleotide having a 6-substituted 9H-purin-9-yl group as a base (e.g., s) is a fluorescent base, and a nucleotide containing the same as a base has strong fluorescence properties.

More specifically, purine derivatives modified to have an expanded electron conjugated system by attaching an aromatic heterocyclic ring or the like at the 6-position are more likely to develop fluorescence properties. Moreover, without being limited thereto, it is previously known that 2-aminopurine has fluorescence properties. Thus, without being limited thereto, purine derivatives having an aromatic heterocyclic ring at the 6-position and an amino group at the 2-position particularly have strong fluorescence properties. In particular, s, s' and v are preferred fluorescent bases. In contrast to conventional techniques, if the fluorescent dye-labeled fifth base can be introduced by transcription at a specific site in a nucleic acid through artificial base pairing, it significantly facilitates the labeling of nucleic acids and hence the analysis and detection of nucleic acids.

The present invention achieves these goals by using an artificial base pair, Pa-s.

The inventors of the present invention fluorescently labeled yeast tRNA$^{Phe}$ in a site-specific manner by using the fluorescent artificial base s as a probe to obtain characteristic fluorescent profiles, depending on the labeling sites, temperature and Mg$^{2+}$ concentration (Example 3). Moreover, the inventors compared these fluorescent profiles with the UV profiles of the same s-labeled yeast tRNA$^{Phe}$. As a result, the following findings were obtained.

First, the melting temperature (Tm value) of each tRNA transcript containing s, obtained from changes in its UV absorption spectrum, was as high as the melting temperature (Tm value) of the natural tRNA transcript, obtained from changes in its UV absorption spectrum. This suggests that the replacement of s at these positions does not significantly destabilize the global tRNA structure.

Second, each tRNA containing s at a specific position showed characteristic fluorescence intensity changes reflecting the local structural features. Namely, in the higher order structure of tRNA, the fluorescence intensity was weak when s stacked with its neighboring bases, whereas the fluorescence intensity increased with decrease in the degree of stacking. This discovery indicates that when s is introduced at a specific position of RNA and then measured, e.g., for temperature-induced changes in its fluorescence intensity, it is possible to know the stacking state of s in the higher order structure. Thus, as an application of s-containing RNA, there is provided a novel method for analyzing the higher order structure of the RNA.

More specifically, the s fluorescent profiles of yeast tRNA$^{Phe}$ in the presence of Mg$^{2+}$ (2 and 5 mM) were clearly divided into two groups. The s fluorescence intensity emitted by Group 1 (tRNA 16s, 17s and 47s) at low temperature was 1.7- to 3.4-fold larger than that of Group 2 (RNA 36s, 57s and 59s). The large intensity emitted by Group 1 decreased when the temperature increased, whereas the intensity of Group 2 increased with increase in temperature. These results suggest that the s bases in Group 1 are exposed to the solution at physiological temperature, and hence the non-specific interaction between s and other bases is increased upon denaturation of the folded structure with increasing temperature. In contrast, the bases in Group 2 stack at low temperature with their neighboring bases in the folded structure, and the base stacking is gradually denatured with increasing temperature. This presumption is entirely consistent with the conformations of the original bases at each site in the crystal structure of tRNA (FIG. 4) (Non-patent Document 20). Moreover, the fluorescence intensity of Group 1 is dramatically increased by addition of Mg$^{2+}$ at physiological temperature. This suggests that tRNA forms an active L-shaped structure in the presence of Mg$^{2+}$, whereby the bases at these positions are kept outside.

Third, the Tm values obtained from the fluorescent profiles reflected the stability of each local structure in the tRNA structure, in comparison with the Tm values obtained from the UV melting profiles.

By way of example, the Tm value obtained from the fluorescent profile of tRNA 36s was higher than that obtained from the UV profile. This suggests that the anticodon stem-loop has a higher stability when compared to the stability of the entire tRNA structure. In contrast, the low stability of tRNA 16s and 17s (low Tm values obtained from the fluorescent profiles) suggests that the partial structure including the D-loop may be a fragile region within the tRNA structure. Thus, when the Tm value of each s-labeled product obtained from its fluorescent profile is compared to that obtained from the UV melting profile, it is possible to determine a degree of stability for each s-labeled local structure.

In this way, site-specific fluorescent probing by using s labels provides a promising tool for studying local structural features of three-dimensional RNA molecules.

Thus, the present invention aims to provide a method for analyzing the stereostructure of a local region in the nucleic acid of the present invention, wherein the local region includes a nucleotide having a 6-substituted 9H-purin-9-yl group as a base. The analysis method of the present invention comprises measuring the fluorescence intensity from the base in the nucleotide having a 6-substituted 9H-purin-9-yl group as a base, under different environmental conditions such as varying temperatures or ion concentrations (e.g., magnesium).

In one embodiment of the analysis method of the present invention, a determination is made that the nucleotide having a 6-substituted 9H-purin-9-yl group as a base stacks with its conformationally neighboring nucleotides at in vivo temperature if the fluorescence intensity from the base in the nucleotide is substantially increased with increase in temperature, or alternatively, a determination is made that the nucleotide is exposed outside at in vivo temperature if the fluorescence intensity is substantially decreased or not increased with increase in temperature.

The term "in vivo temperature" is intended to mean a body temperature when each organism is alive under natural conditions. This temperature varies depending on the type of organisms and ranges from about 35.0° C. to about 39.0° C. for humans, about 36.7° C. to about 39.3° C. for cattle, about 35.0° C. to about 39.0° C. for mice, about 37.9° C. to about 39.9° C. for dogs, and about 38.7° C. to about 39.8° C. for pigs, by way of example.

The expression "nucleotide stacks with its conformationally neighboring nucleotides" is more specifically intended to mean a state where two or more bases stack with each other, preferably within about 5 Å (stacking).

The expression "nucleotide is exposed outside" is more specifically intended to mean a state where the base moiety of the nucleotide does not stack with any other base (preferably located at a distance of about 5 Å or more) or a state where the base moiety is sufficiently apart from a quencher base.

The fluorescence intensity is preferably measured at a specific wavelength where the maximum fluorescence properties are obtained depending on the type of the above 6-substituted 9H-purin-9-yl group. For example, the B1) 2-amino-6-(2-thienyl)-9H-purin-9-yl group (s) shows a fluorescence wavelength with its center at 434 nm when excited at a maximum excitation wavelength of 352 nm. Similarly, the B2) 6-(2-thienyl)-9H-purin-9-yl group (s') shows a fluorescence wavelength with its center at 381 nm when excited at 325 nm, while the B7) 2-amino-6-(2-thiazolyl)-9H-purin-9-yl group (v) shows a fluorescence wavelength with its center at 461 nm when excited at 363 nm.

The expression "fluorescence intensity is substantially increased with increase in temperature" is intended to mean that the fluorescence intensity can be confirmed to increase (e.g., by 1.1-fold or more) when the temperature is increased from 20° C. up to 90° C., by way of example. A greater increase in the fluorescence intensity indicates that the fluorescent base stacks with a larger number of conformationally neighboring nucleotides and/or in closer proximity at in vivo temperature.

The expression "if the fluorescence intensity is substantially decreased or not increased with increase in temperature" is intended to mean that the fluorescence intensity can be confirmed to remain unchanged or to decrease (e.g., by 10% or more) when the temperature is increased from 20° C. up to 90° C., by way of example. A greater decrease in the fluorescence intensity indicates that the fluorescent base exists in more isolation and hence the nucleic acid structure around this base is less likely to take a specific structure at in vivo temperature.

Method for Detecting the Formation of a Nucleic Acid Duplex

The present invention further provides a method for detecting the formation of a nucleic acid duplex, which is another use embodiment of the nucleic acid incorporating a nucleotide having a 6-substituted 9H-purin-9-yl group as a base, which is prepared by the inventive method for preparing a nucleic acid. The detection method of the present invention comprises:

I) inducing hybridization between the following nucleic acids:

i) a nucleic acid incorporating a nucleotide having a 6-substituted 9H-purin-9-yl group as a base, which is prepared by the inventive method for preparing a nucleic acid, and ii) a nucleic acid incorporating a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX); and II) measuring a change in the fluorescence spectrum.

The inventive method for detecting the formation of a nucleic acid duplex is based on fluorescence spectral changes induced by hybridization between a nucleic acid incorporating a nucleotide having a 6-substituted 9H-purin-9-yl group as a base and a nucleic acid incorporating a nucleotide having a 5-substituted-2-oxo(1H)pyridin-3-yl group as a base, whose 5-position is substituted with a fluorescent dye. As described in Patent Documents 1 and 2, Non-patent Document 30 or elsewhere, a 6-substituted 9H-purin-9-yl group (e.g., s or v) can form base pairing with a 2-oxo(1H)pyridin-3-yl group (y). As to synthesis of nucleosides or nucleotides having a 5-substituted-2-oxo(1H)pyridin-3-yl group as a base, details are given in other sections.

When the fluorescence from the 6-substituted 9H-purin-9-yl group and the fluorescence from the 5-substituted-2-oxo(1H)pyridin-3-yl group substituted with a fluorescent dye having different properties are present in the respective two nucleic acid strands, the nucleic acid duplex formation will cause fluorescence resonance energy transfer (FRET) if these fluorescences are in physical proximity to each other, thus producing a change in the fluorescence spectrum. The detection method of the present invention detects the formation of a nucleic acid duplex by measuring a FRET-induced change in the fluorescence spectrum.

The term "fluorescence resonance energy transfer (FRET)" refers to a phenomenon in which the excitation energy is transferred by resonance from one fluorescent molecule to another molecule. A molecule providing energy is referred to as a donor, and a molecule receiving the energy is referred to as an acceptor. Once FRET has occurred, a donor losing its energy returns to the ground state, while an acceptor receiving the energy enters an excited state. Thus, the fluorescence of the donor will become weak and, if the acceptor is a fluorescent molecule, its fluorescence will be observed. If the acceptor is a quencher molecule, the fluorescence observed for the donor alone will not be observed as a result of FRET. Standard techniques for FRET-mediated protein detection and nucleic acid detection are known, including a method for detecting a target protein by introducing two FRET-inducing dyes into RNA aptamers (Jhaveri et al., 2000) and a method for detecting a complementary nucleic acid strand with a hairpin structure (Tyagi et al., 1996). For other information on FRET, see Walter et al., 2001 and Klostermeier et al., 2001.

To cause FRET, the following three requirements should be satisfied. i) The donor's fluorescence spectrum and the acceptor's absorption spectrum should overlap with each other. The overlapping area of their spectra is desirably larger, but they do not necessarily have to completely overlap with each other. The donor's fluorescence spectrum and the acceptor's absorption spectrum preferably overlap in 30% or more, more preferably in 50% or more range. ii) The donor and acceptor should be in a closer physical proximity to each other. The distance at which FRET occurs with 50% probability is recognized to be 3 nm to 6 nm, and the efficiency of FRET sensitively varies in response to a change in this distance. For example, once the nucleic acids have formed a duplex, the nucleotide having a fluorescent 6-substituted 9H-purin-9-yl group as a base is approached by the nucleotide having, as a base, a 5-substituted-2-oxo(1H)pyridin-3-yl group substituted with a fluorescent dye having different properties. If the distance between these nucleotides is preferably 10 nm or less, more preferably 6 nm or less, and most preferably 3 nm or less, it is possible to detect a change in the fluorescence spectrum. iii) The donor and acceptor should be in proper relative orientation to each other.

In one embodiment of the detection method of the present invention, the nucleic acid incorporating a nucleotide having a 5-substituted-2-oxo(1H)pyridin-3-yl group as a base is a nucleic acid incorporating a nucleotide having a 5-substituted-2-oxo(1H)pyridin-3-yl group as a base, whose 5-position is attached to 5-carboxyfluorescein (5-FAM) or 6-carboxyfluorescein (6-FAM) through a linker.

As described above, for example, s has a maximum excitation wavelength of 353 nm and shows a wavelength with its center at 434 nm when excited at a maximum excitation wavelength of 352 nm. On the other hand, FAM has an absorption peak wavelength of 493 nm and a fluorescence peak wavelength of 522 nm. When excited at a wavelength of 353 nm, an s-containing nucleotide will show a wavelength with its center at 434 nm. In contrast, a FAM-substituted nucleotide having a 5-substituted-2-oxo(1H)pyridin-3-yl group as a base (e.g., FAM-y) absorbs the fluorescence from s upon nearing s, and will show a fluorescence spectrum having a fluorescence peak wavelength of 522 nm. Namely, if excitation with a wavelength of 353 nm causes a greater decrease in the 434 nm fluorescence spectrum and a greater increase in the 522 nm fluorescence spectrum, it can be detected that FAM-y is in closer proximity to s, i.e., a nucleic acid duplex is formed through hybridization between s-containing nucleic acid and FAM-y-containing nucleic acid.

Nucleosides or Nucleotides Having a 5-substituted-2-oxo (1H)pyridin-3-yl Group as a Base In nucleosides or nucleotides having a 5-substituted-2-oxo (1H)pyridin-3-yl group as a base, a fluorescent dye is attached either directly or through a linker to the 5-position. These labeled nucleosides or nucleotides are detailed in a preceding patent application filed by the inventors of the present invention (Japanese Patent Application No. 2004-324271, filed on Nov. 8, 2004, not yet published).

As a fluorescent dye, any known dye may be used and is preferably selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX). In general, fluorescein and rhodamine are expressed in both open-ring and spiro forms. These fluorescent dyes are detailed in, e.g., Tuschl et al., 1994; Misra et al., 2004; Gibson et al., 1996; and Chehab et al., 1989.

For example, FAM has an absorption peak wavelength of 493 nm and a fluorescence peak wavelength of 522 nm. Likewise, TAMRA has an absorption peak wavelength of 553 nm and a fluorescence peak wavelength of 578 nm. DANSYL has an absorption peak wavelength of 335 nm and a fluorescence peak wavelength of 518 nm. HEX has an absorption peak wavelength of 535 nm and a fluorescence peak wavelength of 556 nm. TET has an absorption peak wavelength of 521 nm and a fluorescence peak wavelength of 536 nm. 5-ROX has an absorption peak wavelength of 567 nm and a fluorescence peak wavelength of 591 nm. 6-ROX has an absorption peak wavelength of 570 nm and a fluorescence peak wavelength of 590 nm.

Since such a nucleoside or nucleotide having a 5-substituted-2-oxo(1H)pyridin-3-yl group as a base has a fluorescent molecule as a substituent at the 5-position, a nucleic acid may be detected in a manner dependent on the type of fluorescent molecules. Thus, it can be used as a labeled nucleic acid probe to detect substances interacting with the nucleic acid. Moreover, since these individual fluorescent dyes have fluorescent colors different from each other, they can also be used in multiple staining.

The fluorescent dye may be attached either directly or through a linker to the 5-position of the 2-oxo(1H)pyridin-3-yl group. The type of linker is not limited in any way and may be determined as appropriate by those skilled in the art. Without being limited thereto, the linker is preferably selected from the group consisting of chemical formulae I to III shown below:

[Formula 5]

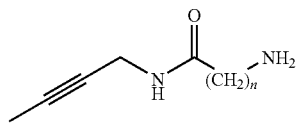

I

[wherein n is selected from integers of 1 to 5];

[Formula 6]

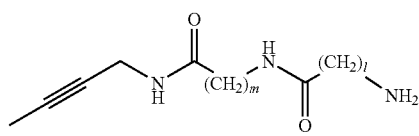

II

[wherein m and l are each independently selected from integers of 1 to 5]; and

[Formula 7]

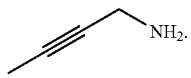

III

Nucleosides or nucleotides having a 5-substituted-2-oxo (1H)pyridin-3-yl group as a base may be synthesized in any manner. 3-(β-D-Ribofuranosyl)-pyridin-2(1H)-one may first be introduced with a substituent at its 5-position and then with triphosphate. Alternatively, 3-(β-D-ribofuranosyl)-pyridin-2 (1H)-one may first be introduced with triphosphate and then with a substituent. In particular, when a large group is introduced, a group such as an aminopropynyl group may first be introduced at the 5-position, to which an activated substituent may then be attached.

Alternatively, such a nucleotide having a 2-oxo(1H)pyridin-3-yl group as a base may be modified with a fluorescent dye not only during synthesis of the nucleotide per se, but also after synthesis of a nucleic acid containing the nucleotide through transcription or the like.

A 5-substituted-2-oxo(1H)pyridin-3-yl group forms two hydrogen bonds with a 6-substituted 9H-purin-9-yl group. The 5-substituted-2-oxo(1H)pyridin-3-yl group cannot form any base pair with natural purine bases A (adenine) and G (guanine) in terms of its stereostructure. Likewise, the 6-substituted 9H-purin-9-yl group cannot form any base pair with natural T (thymine), U (uracil) and C (cytosine) due to steric hindrance. Thus, the 6-substituted 9H-purin-9-yl group (e.g., or v) can specifically form a base pair with the 5-substituted-2-oxo(1H)pyridin-3-yl group.

A nucleotide having a 5-substituted-2-oxo(1H)pyridin-3-yl group as a base can be incorporated into nucleic acids such as DNA or RNA through transcription, replication or reverse transcription reaction. More specifically, when a nucleic acid containing a nucleotide having a 6-substituted 9H-purin-9-yl group as a base, for example, s- or v-containing template DNA is used to effect transcription reaction with T7 RNA polymerase, a substrate of the 2-oxo(1H)pyridin-3-yl group (e.g., yTP) is incorporated into RNA in a site-specific manner, opposite s or v in the template DNA. Since y can be chemically modified at its 5-position, various functional y derivatives can be incorporated into RNA at any specific site.

Alternatively, such a nucleotide having a 5-substituted-2-oxo(1H)pyridin-3-yl group as a base may also be incorporated into DNA or RNA through chemical synthesis, as in the case of nucleosides or nucleotides having natural bases.

Method for Preparing a Nucleic Acid Incorporating Two Artificial Bases on the Same Strand The present invention further aims to provide a method for preparing a nucleic acid incorporating the following nucleotides on the same strand:
  i) a nucleotide having a 6-substituted 9H-purin-9-yl group as a base; and
  ii) a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX).

The preparation method of the present invention comprises effecting transcription, reverse transcription or replication by using, as a template, a nucleic acid incorporating the following nucleotides:
  iii) a nucleotide having a substituted or unsubstituted 2-formyl-1H-pyrrol-1-yl group as a base; and
  iv) a nucleotide having a 6-substituted 9H-purin-9-yl group as a base,
so that the nucleotide of i) is incorporated at a site complementary to the nucleotide of iii), while the nucleotide of ii) is incorporated at a site complementary to the nucleotide of iv).

The above preparation method of the present invention is based on incorporation of a nucleotide having a 6-substituted 9H-purin-9-yl group as a base when a nucleotide having a substituted or unsubstituted 2-formyl-1H-pyrrol-1-yl group as a base is used as a template, in combination with incorporation of a nucleotide having a 5-substituted-2-oxo(1H)pyridin-3-yl group as a base when a nucleotide having a 6-substituted 9H-purin-9-yl group as a base is used as a template.

The present invention further provides such a nucleic acid prepared by the above method, which incorporates the following nucleotides on the same strand:
  i) a nucleotide having a 6-substituted 9H-purin-9-yl group as a base; and
  ii) a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX).

The above nucleic acid of the present invention may be used as tRNA, mRNA, antisense DNA or RNA, a ribozyme, or an aptamer. Moreover, it may also be used in RNA interference (RNAi).

In Example 4 described later, Pa- and v-containing DNA was used as a template to effect transcription, thereby preparing RNA incorporating both s and y or both s and FAM-y on the same strand.

Method for Detecting a Stem-Loop (Hairpin) Structure Formation of Nucleic Acids

The present invention also provides a method for detecting a stem-loop (hairpin) structure formation of the nucleic acid of the present invention incorporating, on the same strand, a nucleotide having a 6-substituted 9H-purin-9-yl group as a base and a nucleotide having a 5-substituted-2-oxo(1H)pyridin-3-yl group as a base. The detection method of the present invention comprises:
  1) inducing hybridization between the nucleotide of i) and the nucleotide of ii) in the nucleic acid of the present invention; and
  2) measuring a change in the fluorescence spectrum.

The method for detecting a stem-loop (hairpin) structure formation of the nucleic acid of the present invention is based on FERT as described herein above in the section "Method for detecting the formation of a nucleic acid duplex." Namely, when the fluorescence from the 6-substituted 9H-purin-9-yl group and the fluorescence from the 5-substituted-2-oxo(1H) pyridin-3-yl group substituted with a fluorescent dye having different properties are present "in the same molecule," the stem-loop (hairpin) formation will cause FRET if these fluorescences are in physical proximity to each other, thus producing a change in the fluorescence spectrum. The detection method of the present invention detects the formation of a stem-loop (hairpin) structure in a nucleic acid by measuring a FRET-induced change in the fluorescence spectrum.

A FRET-induced change in the fluorescence spectrum to detect the formation of a stem-loop (hairpin) structure in a nucleic acid may be observed in the same manner as used for detecting a change in the fluorescence spectrum for two separate nucleic acid strands which form a duplex.

In one preferred embodiment of the present invention, the nucleic acid of the present invention which incorporates a nucleotide having a 6-substituted 9H-purin-9-yl group as a base and a nucleotide having a 5-substituted-2-oxo(1H)pyridin-3-yl group as a base on the same strand makes a stem-loop (hairpin) structure, by the self-complementation between s and FAM-y in its molecule. In this way, by measuring the FRET efficiency between s and FAM-y as probes in the nucleic acid molecule, the higher order structure (e.g., stem-loop structure) of a nucleic acid can be deduced.

Moreover, if a nucleic acid molecule is designed to form a stem-loop (hairpin) structure only when another target molecule is attached thereto, it is possible to create a system for detecting the target molecule based on fluorescence spectral changes. Thus, the present invention is available for use in systems for real-time detection of intermolecular interactions, systems for real-time detection of intramolecular conformational changes, molecular beacons, or intermolecular distance estimation based on FRET efficiency, etc. Such a target molecule includes DNA, RNA, and a protein.

In Example 4 described later, FRET between s and FAM-y was studied for RNA incorporating s and FAM-y on the same strand. In Example 4 described later, when s was excited at 350 nm, FRET was observed and the fluorescence from FAM-y appeared around 521 nm in both cases where a base pair was formed between s and FAM-y through stem-loop formation and where s was apart from FAM-y by addition of a complementary RNA strand to form a double-stranded structure between these molecules. However, when the s fluorescence intensity of a fragment introduced with s and FAM-v (i.e., the intensity around 440 nm in the spectra represented by solid lines in FIGS. 12b and 12c) was compared to the s fluorescence intensity of a control fragment introduced with s and y (i.e., the intensity around 440 nm in the spectra represented by broken lines in FIGS. 12b and 12c), the s fluorescence intensity was found to significantly decrease in a case where a stem-loop structure was formed. The distance between s and FAM-y in this stem-loop structure is 8-10 Å, while the distance between s and FAM-y is increased to 65-67 Å in a double-stranded structure. Thus, a closer distance between s and FAM-y provides an increased FRET efficiency between them.

Nucleic Acids Incorporating Two or More Adjacent Nucleotides Having a 6-substituted 9H-purin-9-yl Group as a Base Nucleic acids incorporating two or more adjacent nucleotides having a 6-substituted 9H-purin-9-yl group as a base also fall within the scope of the present invention.

In the above nucleic acids, since two or more nucleotides having a 6-substituted 9H-purin-9-yl group as a base are located adjacent to each other on the same strand, self-quenching occurs between these adjacent artificial bases to cause a significant decrease in the fluorescence intensity of the 9H-purin-9-yl groups, as compared to a case where nucleotides having a 9H-purin-9-yl group as a base are not located adjacent to each other (see FIGS. 13c and 13d). On the other hand, even where self-quenching occurs between 9H-purin-9-yl groups, hybridization with a 5-substituted-2-oxo(1H) pyridin-3-yl group whose 5-position is substituted with a fluorescent dye permits FRET between a 9H-purin-9-yl group and the fluorescent dye (see FIGS. 14c and 14d). Moreover, in the nucleic acids incorporating two or more adjacent nucleotides having a 6-substituted 9H-purin-9-yl group as a base, the fluorescence intensity of the 9H-purin-9-yl groups is decreased, i.e., the background fluorescence is low, thus allowing efficient observation of FRET with a fluorescent dye (see FIG. 15). Namely, the FRET system of the present invention which uses a self-quenched probe containing two or more adjacent nucleotides having a 6-substituted 9H-purin-9-yl group as a base can keep the background of the fluorescent donor at a low level and is therefore particularly useful in allowing detection of complementary strands containing a fluorescent acceptor even in the presence of excessive donor probe.

Such a nucleic acid incorporating two or more adjacent nucleotides having a 6-substituted 9H-purin-9-yl group as a base is available for use in the above method for detecting the formation of a nucleic acid duplex or the above method for detecting a stem-loop or hairpin structure formation of a nucleic acid.

In such a nucleic acid incorporating two or more adjacent nucleotides having a 6-substituted 9H-purin-9-yl group as a base, there is no particular limitation on the number of adjacent nucleotides having a 6-substituted 9H-purin-9-yl group as a base as long as it is two or more. The number of these adjacent nucleotides is preferably 2 to 10, 2 to 5, 2 to 3, and most preferably 2.

Such a nucleic acid incorporating two or more adjacent nucleotides having a 6-substituted 9H-purin-9-yl group as a base may be prepared, but not limited to, by the inventive method for preparing a nucleic acid or through known chemical synthesis procedures.

EFFECTS OF THE INVENTION

According to the present invention, the discovery of new base pairing between unnatural bases Pa and s has suggested that shape complementarity between paired bases is also important during transcription (Non-patent Documents 5-6). This enables the incorporation of a nucleotide having a 6-substituted 9H-purin-9-yl group as a base during transcription, although such incorporation has previously been difficult to achieve during transcription.

The method of the present invention achieves significantly higher yields than other methods previously known for obtaining RNA having s at a desired position(s): (1) chemical RNA synthesis; (2) transcription reaction using template DNA having a y nucleotide(s); and (3) transcription reaction using template DNA having a nucleotide(s) having a 2-oxo-1,3-dihydro-imidazol-1-yl group (z).

Conventional fluorescent probes such as commonly-used 2-aminopurine nucleotides (Non-patent Documents 21-23) cannot be incorporated through transcription into RNA in a site-specific manner, and hence they are particularly difficult to use in long-chain RNA molecules. Namely, in the prior art methods, a nucleotide derivative of 2-aminopurine is introduced into RNA through chemical synthesis. However, long-chain RNA (50 nucleotides or longer) is difficult to synthesize through chemical RNA synthesis, and the operations required are also complicated and time-consuming. Thus, the prior art methods were of limited application.

In contrast, the present invention enables the site-specific incorporation of a nucleotide having a fluorescent 6-substituted 9H-purin-9-yl group as a base into RNA. Although DNA serving as a template is required to be chemically synthesized in the present invention, chemical synthesis of DNA allows synthesis of longer molecules (around 150 nucleotides) when compared to RNA synthesis, and the chemically synthesized DNA molecules can also be linked together by the action of enzymes. This particularly enables the analysis of long-chain RNA, which is impossible to achieve by conventional fluorescence probing techniques. This may provide a powerful tool for studying the dynamics of local conformational changes at a defined position within a large RNA molecule. In Example 3 of the present invention, a local higher order structure (stacking) within tRNA was actually analyzed.

Moreover, RNA molecules have now been found to have many new functions (e.g., RNA interference) in the body, and the development of drugs based on such phenomena has also proceeded. However, not many techniques exist for studying in vivo behavior of these RNA molecules. Thus, this fluorescence probing technique provides a good method for in vivo analysis of RNA and for studying in vivo kinetics of RNA drugs.

Furthermore, the s-Pa base pair newly found by the present invention enables the site-specific incorporation of amino acid analogs into proteins through translation, and hence can be put to practical use in expanding the genetic code (Non-patent Document 15).

BRIEF DESCRIPTION OF THE DRAWINGS

FIG. 2A: Experimental scheme

FIG. 2B: Gel electrophoresis of transcripts obtained by using template DNA containing one or two Pa or z bases in the presence of natural NTPs (1 mM) and sTP (1 mM). The transcripts were labeled with [γ-$^{32}$P]GTP at their 5'-end. The relative yield of each transcript was determined in comparison with the yield of a transcript from a template composed only of natural bases, and each yield was averaged from 3 to 4 data sets.

FIG. 4 shows the secondary structure of the original tRNA transcript. The positions replaced by s are circled. Each wavy line represents base-base interaction in the tertiary structure. Although the boxed G-C pair was changed from the original C-G pair, this mutation does not significantly alter the original tRNA structure (Non-patent Document 26).

FIG. 5 shows the tertiary structure of the original tRNA transcript.

FIG. 10 shows procedures for site-specific introduction of y and s into RNA through transcription using v-y and s-Pa base pairing, along with the results of polyacrylamide electrophoresis on the transcripts. In FIG. 10a, P in the sequences represents an artificial base Pa.

FIG. 12 shows the results of fluorimetry on RNA (Bhp2-1) introduced with artificial bases s and y or FAM-y. FIG. 12b shows the fluorescence spectrum of Bhp2-1 which forms a duplex with its complementary RNA. FIG. 12c shows the results of Bhp2-1 which remains in a single-stranded state to thereby form a hairpin structure. In each of FIGS. 12b and 12c, the solid line represents the results of Bhp2-1 having FAM-y at position 13 and s at position 36, while the wavy line represents the results of Bhp2-1 having y at position 13 and s at position 36.

EXAMPLES

Figure 1:
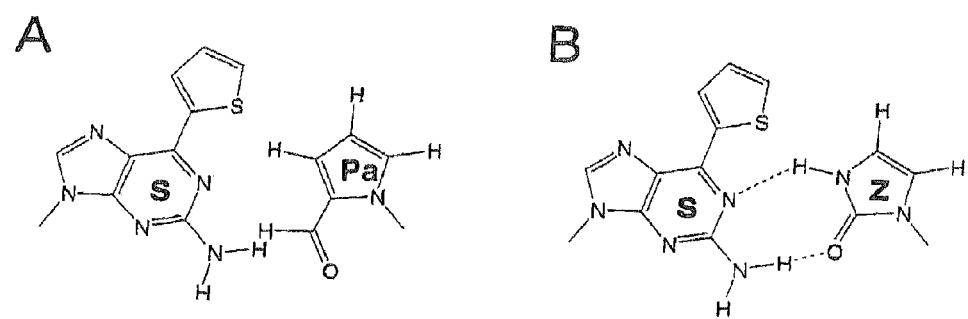
FIG. 1 shows unnatural s-Pa (A) and s-z (B) base pairs.

The present invention will now be further described in the following examples, which are not intended to limit the technical scope of the invention. Based on the detailed description, various changes and modifications will be apparent to those skilled in the art, and such changes and modifications fall within the technical scope of the invention.

Example 1

T7 Transcription Through s-Pa Base Pairing

In this example, T7 transcription was performed through s-Pa base pairing.

1) Reagents, Solvents and Others

All reagents and solvents were purchased from usual suppliers and were used without further purification. Electrospray-ionization mass spectra (ESI-MS) were recorded on a Waters ZMD 4000 LC/MS system. DNA templates were chemically synthesized using phosphoramides of Pa (Non-patent Document 9) and natural bases in an automated DNA synthesizer (model 392, PerkinElmer Applied Biosystems, Foster City, Calif.). Gel electrophoresis was used for purification of oligonucleotides.

2) Synthesis of 2-amino-6-(2-thienyl)-9-(1-β-D-ribofuranosyl)purine 5'-triphosphate (sTP)

2-N-Phenoxyacetyl-6-(2-thienyl)-9-(2,3-di-O-acetyl-1-β-D-ribofuranosyl)purine (57 mg, 0.1 mmol) (Non-patent Document 29) was dissolved in pyridine and then evaporated in vacuo to remove the solvent together with water contained therein. The residue was dissolved in pyridine (100 µl) and dioxane (300 µl), followed by addition of a 1 M dioxane solution (100 µl) of 2-chloro-4H-1,2,3-benzodioxaphosphorin-4-one (0.11 mmol) (Non-patent Document 25). After 10 minutes, this solution was quickly mixed with a 0.5 M DMF solution (300 µl) of bis(tributylammonium)pyrophosphoric acid (0.15 mmol) and with tri-n-butylamine (100 µl). The reaction mixture was stirred at room temperature for 10 minutes, followed by addition of a 1% iodine solution (in pyridine/water (98:2, v/v), 2 ml). After 15 minutes, the reaction solution was supplemented with a 5% aqueous $NaHSO_3$ solution (150 µl) and then with water (5 ml).

The solution was stirred at room temperature for 30 minutes, followed by addition of concentrated aqueous ammonia (20 ml). Ammonolysis was performed at 55° C. for 12 hours. The solution was concentrated in vacuo, and the product was purified by DEAE sephadex (A-25) column chromatography (eluted with a linear gradient of 50 mM to 1 M TEAB) and then by C18-HPLC (eluted with a gradient of 0% to 30% $CH_3CN$ in 100 mM triethylammonium acetate using a Gilson HPLC purification system with a Synchropak RPP (Eichorom Technologies)) to obtain sTP.

[Formula 8]

$^1$H NMR (270 MHz, $D_2O$) δ 1.13 (t, 27H, J=7.3 Hz), 3.05 (q, 18H, J=7.3 and 14.8 Hz), 4.19 (m, 2H), 4.32 (m, 1H), 4.56 (m, 1H), 4.83 (m, 1H), 5.94 (d, 1H, J=5.9 Hz), 7.19 (dd, 1H, J=4.0 and 4.9 Hz), 7.66 (d, 1H, J=4.9 Hz), 8.16 (d, 1H, J=4.0 Hz), 8.33 (s, 1H).

$^{31}$P NMR (109 MHz, $D_2O$) 8-22.38 (t, 1H, J=19.5 and 20.1 Hz), −10.68 (d, 1H, J=19.5 Hz), −9.24 (d, 1H, J=20.1 Hz).

ESI-MS for $C_{14}H_{17}N_5O_{13}P_3S$ (M-H): calcd, 587.98; found, 587.70.

3) Preparation of Templates for T7 Transcription

Chemically synthesized DNA templates (10 µM 35-mer coding strand and 21-mer non-coding strand for 17-mer RNA synthesis) were each annealed in 10 mM Tris-HCl (pH 7.6) buffer containing 10 mM NaCl by heating at 95° C. and then slow cooling to 4° C.

4) T7 Transcription (17-mer RNA)

Transcription was performed in a 40 mM Tris-HCl (pH 8.0) buffer solution (20 µl) containing 24 mM $MgCl_2$, 2 mM spermidine, 5 mM DTT and 0.01% Triton X-100, in the presence of 1 mM natural NTPs or 1 mM sTP, 2 µCi [γ-$^{32}$P] GTP, 2 µM template and 50 units of T7 RNA polymerase (Takara, Kyoto).

The use of [γ-$^{32}$P]GTP allowed determination of yields because the transcripts were labeled only at their 5'-end. After incubation at 37° C. for 3 hours, a dye solution (20 µl) containing 10 M urea and 0.05% BPB was added to stop the reaction. The mixtures were each heated at 75° C. for 3 hours and the products were analyzed on a 20% polyacrylamide-7 M urea gel.

5) Results

In this example, transcription was accomplished by using s (sTP) as a substrate and by using DNA templates containing one or two Pa bases such that the unnatural base(s) is/are located at a complementary position(s) corresponding to positions 13 to 15 of the transcript. FIG. 2A shows the experimental scheme. In FIG. 2A, the sequences of 10 μM 35-mer coding strand and 21-mer non-coding strand for 17-mer RNA synthesis, as well as the nucleotide sequence of the 17-mer RNA transcript are as shown below.

```
Template complementary strand
                                        (SEQ ID NO: 1)
5'-ataatacgactcactataggg-3'

Template strand
                                        (SEQ ID NO: 2)
3'-tattatgctgagtgatatccctcgaagggannntc-5'

17-mer RNA transcript
                                        (SEQ ID NO: 3)
5'-gggagcuucccunnnag-3'
```

The inventors of the present invention also studied additional DNA templates containing imidazophosphorin-2-one (z) (FIG. 1B) as controls (FIG. 1B); z is a good template base for site-specific insertion of s into RNA through T7 transcription, but its transcription efficiency is low when compared to natural transcription. Although the s-z pair may form two hydrogen bonds between bases, its configuration is similar to that of the s-Pa pair.

These templates were used to effect transcription for 3 hours, and the transcripts whose 5'-end was labeled with [γ-$^{32}$P]GTP were analyzed on a gel. The results obtained are shown in FIG. 2B. More specifically, FIG. 2B shows the results of gel electrophoresis on the products transcribed using the templates containing one or two Pa or z bases in the presence of natural NTPs (1 mM, N=A, G, C, U) and sTP (1 mM). The transcripts are labeled with [γ-$^{32}$P]GTP at their 5'-end. The relative yield of each transcript was determined in comparison with the yield of a transcript from a template composed only of natural bases, which was set to 100%. Each yield was averaged from 3 to 4 data sets.

As shown in FIG. 2B, the full-length (17-mer) transcript (containing one s base) obtained from template DNA containing one Pa base was found to have a relative yield of 92% (FIG. 2B, Lane 1, $N_1$=Pa), which was higher than the yield of transcription from template DNA containing one z base (35%, FIG. 2B, Lane 4), and was as high as the yield of transcription using a template composed only of natural bases ($N_1$=C) and NTPs (FIG. 2B, Lane 8). In the case of transcription using a template containing two Pa bases, the relative yield was low when compared to natural transcription (FIG. 2B, Lane 8), but full-length products were obtained (FIG. 2B, Lanes 2 and 3). In contrast, in the case of transcription using a template containing two z bases, no full-length transcript was obtained (FIG. 2B, Lanes 5 and 6).

Example 2

Composition Analysis of Nucleotides in T7 Transcripts (17-mer RNAs)

In this example, to study the selectivity of s-Pa base pair during transcription, composition analysis was performed on nucleotides in the full-length (17-mer) transcripts obtained by transcription from Pa, z and natural templates. The transcripts were each internally labeled with any of [α-$^{32}$P]UTP, [α-$^{32}$P]ATP or [α-$^{32}$P]GTP, and these transcripts were completely digested with RNase $T_2$ into a nucleoside 3'-phosphate form. The resulting labeled nucleotides were analyzed by 2D-TLC (FIG. 3), and the spots were quantified for each nucleoside 3'-monophosphate (Table 1).

More specifically, transcription was performed in 40 mM Tris-HCl (pH 8.0) buffer (20 μl) containing 24 mM $MgCl_2$, 2 mM spermidine, 5 mM DTT and 0.01% Triton X-100, in the presence of 10 mM GMP, 1 mM natural NTPs (1 mM, N=A, G, C, U), 0, 1 or 3 mM sTP, 2 μCi [γ-$^{32}$P]UTP, [γ-$^{32}$P]ATP or [γ-$^{32}$P]GTP (Amersham), 2 μM template DNA, and 50 units of T7 RNA polymerase (Takara) (Non-patent Documents 14 and 15). After incubation for 3 hours at 37° C., a dye solution was added to stop the transcription.

This mixture was heated at 75° C. for 3 hours and then electrophoresed on a 15% polyacrylamide-7 M urea gel. The full-length product was eluted from the gel and 0.05 $A_{260}$ units of E. coli tRNA was then added thereto, followed by ethanol precipitation. The transcript was digested at 37° C. for 2 hours with 0.075 U/μl RNase $T_2$ in 15 mM sodium acetate buffer (pH 4.5). By this treatment, the transcript was completely digested into nucleoside 3'-monophosphates by the action of RNase $T_2$. The digestion products were analyzed by 2D-TLC using a Merck HPTLC plate (100×100 mm, Merck, Darmstadt, Germany). The developing solvents used for the first and second dimensions were isobutyric acid/$NH_4OH$/$H_2O$ (66:1:33 v/v/v) and isopropyl alcohol/HCl/$H_2O$ (70:15:15 v/v/v), respectively. The products on the TLC plate were analyzed with a bio-imaging analyzer. Each spot was quantified by averaging from 3 to 9 data sets.

Figure 3:
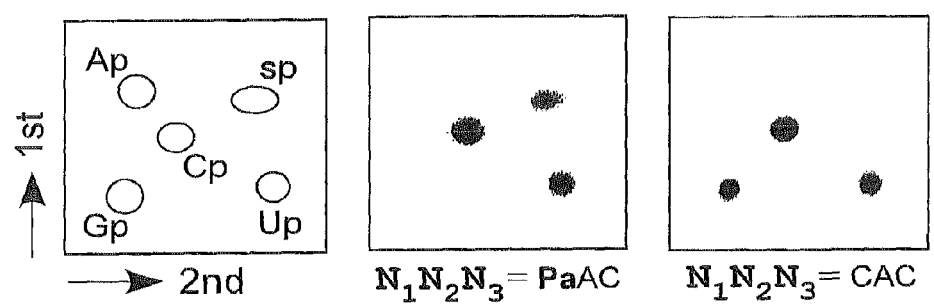
FIG. 3 shows 2D-TLC analysis of the labeled ribonucleoside 3'-monophosphates obtained from nuclease digestion of the transcripts (17-mer). The transcripts were internally labeled with [α-$^{32}$P]NTP, and two-dimensional TLC was obtained from the 17-mer fragments transcribed in the presence of 1 mM sTP. $N_1N_2N_3$ in template DNA is PaAC in the middle panel, while $N_1N_2N_3$ is CAC in the right panel.

The results obtained are shown in FIG. 3. Further, the quantification results for each nucleoside 3'-monophosphate are summarized in Table 1.

TABLE 1

| | | | | Nucleotide composition analysis of T7 transcripts | | | | |
|---|---|---|---|---|---|---|---|---|
| | | | | Composition of nucleotides incorporated at 5' neighbor of U, A or G$^a$ | | | | |
| Entry No. | Template $N_1N_2N_3$ | [α-$^{32}$P] NTP | sTP (mM) | Ap | Gp | Cp | Up | sp |
| 1 | PaAC | UTP | 1 | 0.01$^b$ [0]$^c$ (0.01)$^d$ | n.d. [0] (<0.01) | 1.99 [2] (0.05) | 1.02 [1] (0.03) | 0.97 [1] (0.03) |
| 2 | zAC | UTP | 1 | 0.01 [0] (<0.01) | 0.01 [0] (0.01) | 1.99 [2] (0.02) | 1.02 [1] (0.05) | 0.97 [1] (0.05) |
| 3 | CAC | UTP | 0 | 0.01 [0] (<0.01) | 0.97 [1] (0.03) | 2.02 [2] (0.02) | 1.01 [1] (0.03) | n.d.$^e$ [0] (—) |
| 4 | CAC | UTP | 1 | 0.01 [0] (<0.01) | 0.98 [1] (0.02) | 2.03 [2] (0.03) | 0.99 [1] (0.04) | n.d. [0] (—) |
| 5 | TAC | UTP | 0 | 1.00 [1] (0.03) | 0.01 [0] (<0.01) | 2.02 [2] (0.01) | 0.97 [1] (0.04) | n.d. [0] (—) |
| 6 | TAC | UTP | 1 | 1.00 [1] (0.03) | 0.01 [0] (<0.01) | 2.01 [2] (0.01) | 0.97 [1] (0.03) | 0.01 [0] (<0.01) |

TABLE 1-continued

Nucleotide composition analysis of T7 transcripts

| Entry No. | Template $N_1N_2N_3$ | $[\alpha\text{-}^{32}P]$ NTP | sTP (mM) | Composition of nucleotides incorporated at 5' neighbor of U, A or G$^a$ | | | | |
|---|---|---|---|---|---|---|---|---|
| | | | | Ap | Gp | Cp | Up | sp |
| 7 | PaAPa | UTP | 1 | 0.01 [0] (0.01) | 0.01 [0] (<0.01) | 2.03 [2] (0.03) | 1.00 [1] (0.02) | 0.95 [1] (0.03) |
| 8 | PaAPa | UTP | 3 | 0.01 [0] (0.01) | 0.01 [0] (0.01) | 2.01 [2] (0.01) | 0.99 [1] (0.01) | 0.98 [1] (0.01) |
| 9 | PaAPa | ATP | 1 | 0.05 [0] (<0.01) | 1.06 [1] (0.07) | n.d. [0] (—) | 0.01 [0] (<0.01) | 0.87 [1] (0.07) |
| 10 | PaAPa | ATP | 3 | 0.04 [0] (0.01) | 1.02 [1] (0.06) | n.d. [0] (—) | 0.01 [0] (<0.01) | 0.93 [1] (0.07) |
| 11 | CAC | ATP | 1 | 0.03 [0] (<0.01) | 1.95 [2] (0.01) | n.d. [0] (—) | 0.02 [0] (0.01) | n.d. [0] (—) |
| 12 | CAC | ATP | 3 | 0.03 [0] (<0.01) | 1.94 [2] (0.01) | n.d. [0] (—) | 0.02 [0] (0.01) | n.d. [0] (—) |
| 13 | PaPaC | GTP | 1 | 1.99 [2] (0.05) | 1.15 [1] (0.05) | 0.02 [0] (0.02) | n.d. [0] (—) | 0.84 [1] (0.03) |
| 14 | PaPaC | GTP | 3 | 1.94 [2] (0.03) | 1.13 [1] (0.07) | 0.02 [0] (0.01) | 0.01 [0] (0.02) | 0.89 [1] (0.10) |
| 15 | CAC | GTP | 1 | 1.98 [2] (0.06) | 1.01 [1] (0.03) | 0.01 [1] (0.01) | 1.98 [2] (0.08) | 0.01 [1] (0.01) |
| 16 | CAC | GTP | 3 | 1.99 [2] (0.04) | 0.99 [1] (0.03) | 0.01 [0] (0.01) | 1.99 [2] (0.08) | 0.02 [1] (0.01) |

Figure 2:
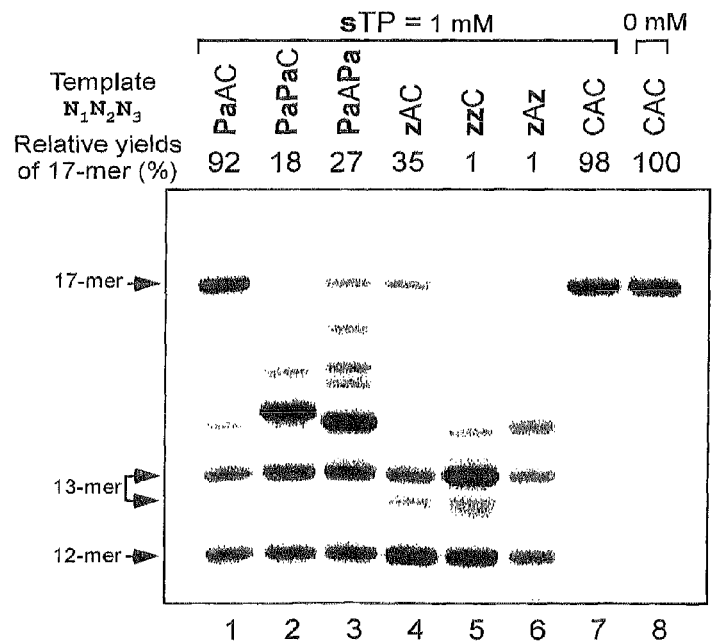
FIG. 2 shows an experimental scheme for T7 transcription mediated by s-Pa base pairing, along with the results of gel electrophoresis on the transcripts.

$^a$Composition of nucleotides incorporated at the 5'-side of U (Entry Nos. 1-8), A (Entry Nos. 9-12) or G (Entry Nos. 13-16) in the transcripts shown in FIG. 2
$^b$The values were determined by using the following equation. (Radioactivity of each nucleotide)/[All nucleotides (3'-monophosphates)] × (Total number of nucleotides at 5'-side of [$\alpha\text{-}^{32}P$]NTP]
$^c$The theoretical number of each nucleotide is shown in square brackets.
$^d$The standard deviation is shown in parentheses.
$^e$Not detected The results shown in FIG. 3 and Table 1 confirmed that was incorporated into RNA with high selectivity when using the template containing one Pa base. In FIG. 3, only when using the Pa-containing template and labeling with [γ-$^{32}$P]UTP, the labeled s-nucleoside 3'-monophosphate was observed on 2D-TLC. Moreover, as shown in Table 1, the selectivity (97%) of s incorporation into RNA opposite Pa in the template DNA (Table 1, Entry No. 1) was as high as the selectivity through s-z base pairing (Table 1, Entry No. 2) or the selectivity of transcription through natural base pairing (Table 1, Entry Nos. 3 and 5), and there was no misincorporation of sTP opposite natural bases in the template (Table 1, Entry Nos. 4 and 6). In the case of transcription using a template containing two Pa bases, the selectivity of s incorporation at the first position was sufficiently high (95%), while the selectivity of s incorporation at the second position was about 84-87%. However, this selectivity was improved somewhat (89-93%) by increasing the sTP concentration (3 mM). Thus, Pa is superior to z as a template base for use in site-specific incorporation of s into RNA, and this result suggests that non-hydrogen-bonded base pairs may also be functional during transcription.

Example 3

Preparation of 16s, 17s, 36s, 47s, 57s and 59s tRNAs and Their Fluorescence Spectra and UV Melting Curves 1) Preparation of 16s, 17s, 36s, 47s, 57s and 59s tRNAs To prove the usefulness of the s base as a fluorescent probe, the inventors of the present invention incorporated s at a specific site in yeast tRNA$^{Phe}$ and then analyzed the fluorescence properties of s at each site in the tRNA under various conditions to thereby study the higher order structure of the tRNA. Since the fluorescence of the s base is quenched by stacking with its neighboring bases, information is obtained on the local structure around s in RNA molecules.

Figure 4:
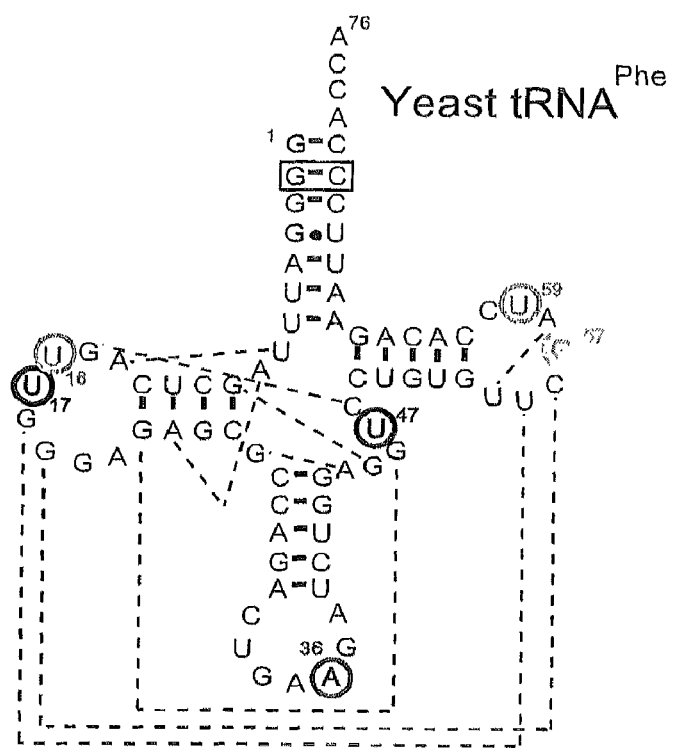
FIG. 4 shows the introduction sites for s in yeast tRNA$^{Phe}$, along with the structure of the tRNA (Non-patent Document 20).

The inventors of the present invention introduced s at the following 6 sites in the tRNA, separately: position 16 or 17 in the D-loop (tRNA 16s or 17s), position 36 in the anticodon (tRNA 36s), position 47 in the extra-loop (tRNA 47s), and position 57 or 59 in the TΨC-loop (tRNA 57s or 59s). s at each site is introduced at a site which is not used for base pairing with other bases in the tRNA (FIG. 4).

The sequences of each template for preparing s-containing yeast tRNA$^{Phe}$ molecules (5 μM 94-mer template strand DNA and its complementary strand DNA for RNA synthesis) are as shown in Table 2 below (SEQ ID NOs: 4-11).

TABLE 2

1. Sequences of DNA templates for s-containing tRNA transcripts.

Non-template strand (94-mer) for all tRNA transcripts
(SEQ ID NO: 4)
ATAATACGACTCACTATAGGGGATTTAGCTCAGTTGGGAGAGCGCCAGAC
TGAAGATCTGGAGGTCCTGTGTTCGATCCACAGAATTCCCACCA Template strand (94-mer) for the original tRNA
transcript (Tm = 2'-OMe-T, Gm = 2'-OMe-G)
(SEQ ID NO: 5)
TmGmGTGGGAATTCTGTGGATCGAACACAGGACCTCCAGATCTTCAGTCT
GGCGCTCTCCCAACTGAGCTAAATCCCCTATAGTGAGTCGTATTAT Template strand (94-mer) for tRNA 16s (Tm = 2'-OMe-T, Gm = 2'-OMe-G)
(SEQ ID NO: 6)
TmGmGTGGGAATTCTGTGGATCGAACACAGGACCTCCAGATCTTCAGTCT
GGCGCTCTCCCAPaCTGAGCTAAATCCCCTATAGTGAGTCGTATTAT

TABLE 2-continued

1. Sequences of DNA templates for s-containing tRNA transcripts.

Template strand (94-mer) for tRNA 17s (Tm = 2'-OMe-T, Gm = 2'-OMe-G)
(SEQ ID NO: 7)
TmGmGTGGGAATTCTGTGGATCGAACACAGGACCTCCAGATCTTCAGTCT
GGCGCTCTCCCPaACTGAGCTAAATCCCCTATAGTGAGTCGTATTAT Template strand (94-mer) for tRNA 36s (Tm = 2'-OMe-T, Gm = 2'-OMe-G)
(SEQ ID NO: 8)
TmGmGTGGGAATTCTGTGGATCGAACACAGGACCTCCAGATCPaTCAGTC
TGGCGCTCTCCCAACTGAGCTAAATCCCCTATAGTGAGTCGTATTAT Template strand (94-mer) for tRNA 47s (Tm = 2'-OMe-T, Gm = 2'-OMe-G)
(SEQ ID NO: 9)
TmGmGTGGGAATTCTGTGGATCGAACACAGGPaCCTCCAGATCTTCAGTC
TGGCGCTCTCCCAACTGAGCTAAATCCCCTATAGTGAGTCGTATTAT Template strand (94-mer) for tRNA 57s (Tm = 2'-OMe-T, Gm = 2'-OMe-G)
(SEQ ID NO: 10)
TmGmGTGGGAATTCTGTGGATPaGAACACAGGACCTCCAGATCTTCAGTC
TGGCGCTCTCCCAACTGAGCTAAATCCCCTATAGTGAGTCGTATTAT Template strand (94-mer) for tRNA 59s (Tm = 2'-OMe-T, Gm = 2'-OMe-G)
(SEQ ID NO: 11)
TmGmGTGGGAATTCTGTGGPaTCGAACACAGGACCTCCAGATCTTCAGTC
TGGCGCTCTCCCAACTGAGCTAAATCCCCTATAGTGAGTCGTATTAT Sequences of 5 µM 94-mer template DNA and its complementary strand DNA for RNA synthesis In these sequences, the C2-G71 base pair is replaced by G2-C71 (Non-patent Document 26). Two nucleosides (G and T) at the 5'-end of each template strand DNA are replaced by 2'-O-methylribonucleosides to thereby prevent template-independent production of transcripts which are longer than the desired product (Non-patent Document 27).

Preparation of 94-mer template DNA and its complementary strand DNA for RNA synthesis was accomplished in the same manner as described in Example 1, the section "3) Preparation of templates for T7 transcription."

Figure 5:
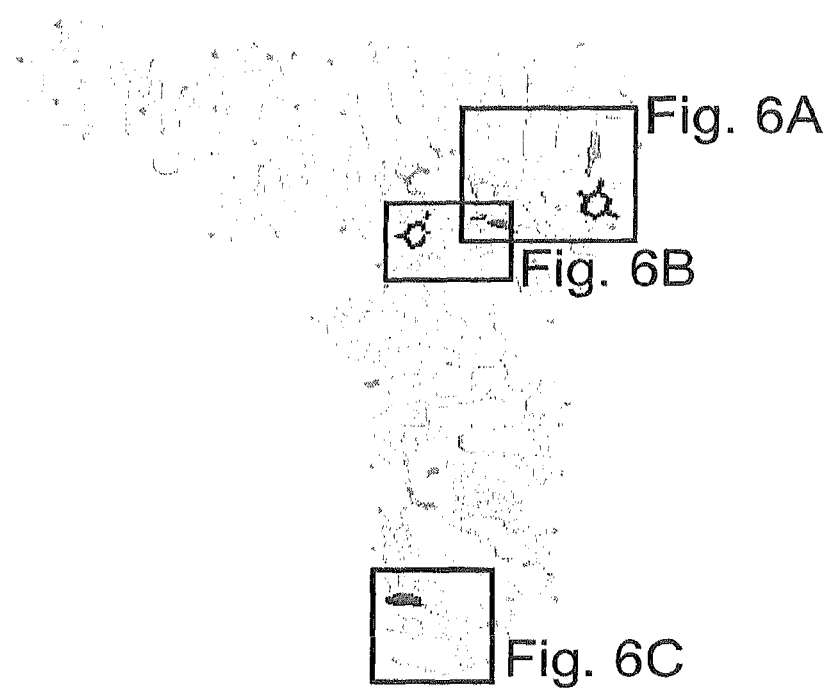
FIG. 5 shows the introduction sites for s in yeast tRNA$^{Phe}$, along with the structure of the tRNA (Non-patent Document 20).
Figure 6:
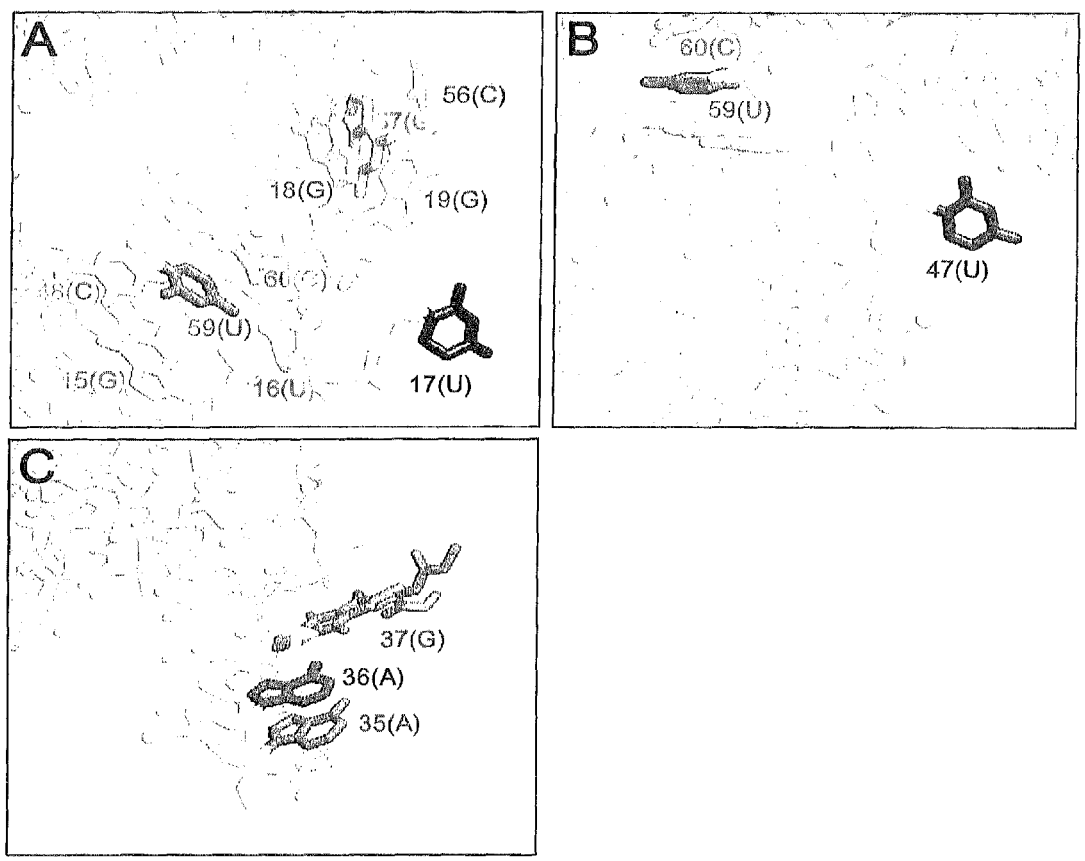
FIGS. 6A to 6C each show a magnified view of a region covering the introduction sites for s in yeast tRNA$^{Phe}$. The dark-colored bases are at sites for replacement by s and stack with light-colored bases. Spheres (yellow) each represent $Mg^{2+}$. Although bases shown in the figures are modified bases, the bases in parentheses correspond to those in the original transcript.

FIGS. 4 to 6 show the introduction sites for s in yeast tRNA$^{Phe}$, along with tRNA structures (Non-patent Document 20). FIG. 4 shows the secondary structure of the original tRNA. The bases replaced by s are circled. Each wavy line represents base-base interaction. The boxed G-C base pair corresponds to the C-G base pair in the original tRNA, and this replacement does not significantly alter the higher order structure of the tRNA (Non-patent Document 26).

FIG. 5 shows the tertiary structure of the natural tRNA, while FIGS. 6A to 6C each show a magnified view of each site where s is incorporated. The dark-colored bases are replaced by s and stack with light-colored bases. Spheres (yellow) each represent $Mg^{2+}$ in the tRNA. Although bases shown in the figures are those modified in the natural tRNA, the bases in parentheses represent those in the transcripts.

tRNA transcripts incorporating s at the respective sites were each prepared with T7 RNA polymerase using Pa-containing template DNA in the presence of 1 mM sTP and natural NTPs. More specifically, in 40 mM Tris-HCl (pH 8.0) buffer containing 24 mM $MgCl_2$, 2 mM spermidine, 5 mM DTT and 0.01% Triton X-100, transcription was first performed in the presence of 10 mM GMP, 1 mM natural NTPs, 1 mM sTP, 0.5 µM template DNA and 2.5 U/µl T7 RNA polymerase. After incubation at 37° C. for 6 hours, 1.75 volumes of a dye solution was added to stop the transcription. This solution was heated at 75° C. for 3 minutes and then electrophoresed on a 10% polyacrylamide-7 M urea gel. The full-length product was eluted from the gel and precipitated with ethanol. The product was dissolved in 450 µl of 10 mM EDTA (pH 8) and incubated at 75° C. for 5 minutes.

By using a Microcon YM-10 filter (Amicon), the buffer solution was then replaced by a buffer for Tm measurement (containing 50 mM sodium cacodylate (pH 7.2) and 50 mM KCl). The amount of tRNA was determined by absorbance at 260 nm. For fluorescence and UV melting measurement, a solution was prepared to contain 1 µM tRNA in Tm buffer containing 0.1 mM EDTA, 2 mM $MgCl_2$ or 5 mM $MgCl_2$.

2) Fluorescence Spectra and UV Melting Curves

A fluorescence spectrum and a UV melting curve were recorded for each tRNA containing s at a specific site, in the range of 20° C. to 90° C. at a heating rate of 0.5° C./minute by using an FP-6500 spectrofluorometer (JASCO) and a UV-2450 spectrophotometer (SHIMADZU), respectively.

Figure 7:
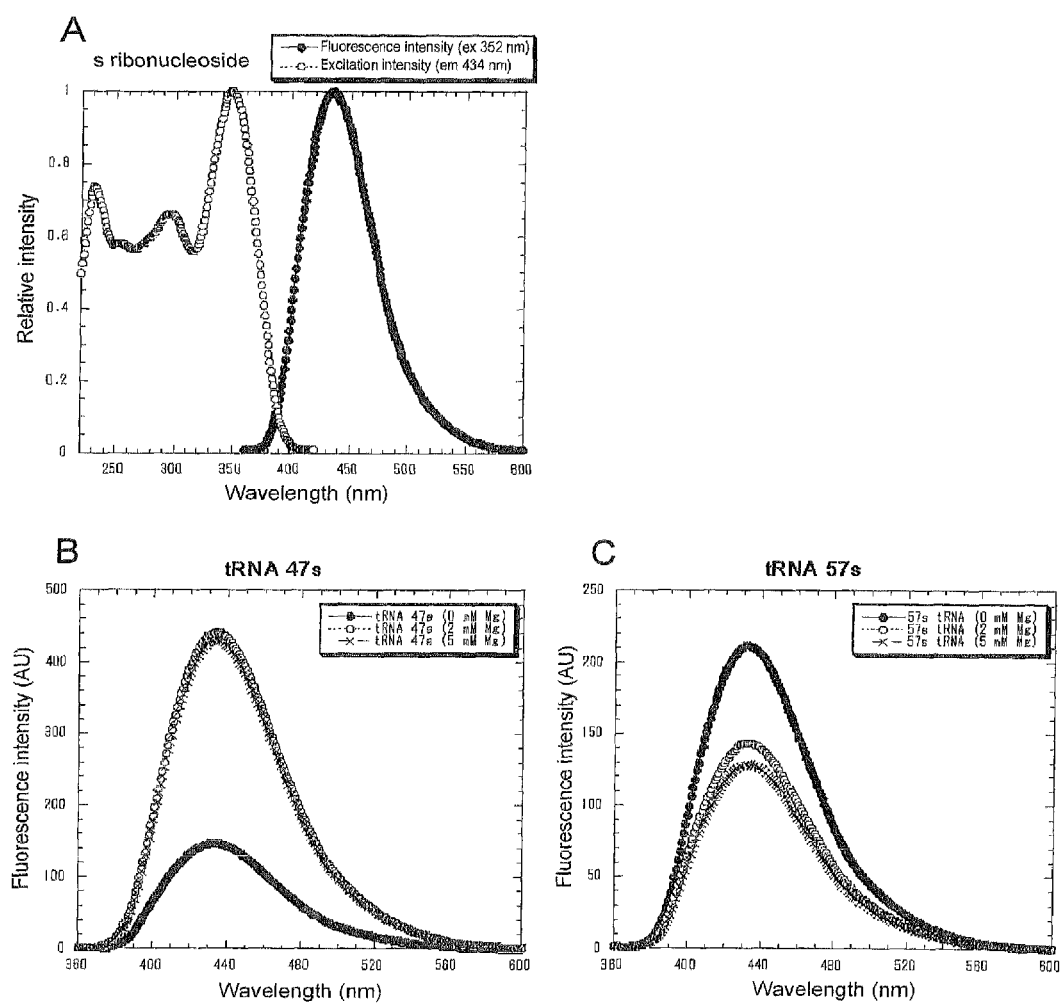
FIG. 7A shows the excitation and fluorescence spectra of s ribonucleoside (1 μM). The solid line with solid circles represents the fluorescence spectrum with excitation at 352 nm. The wavy line with open circles represents the fluorescence spectrum with excitation at 434 nm.
FIGS. 7B and 7C show the fluorescence spectra of tRNA 47s (1 μM) and tRNA 57s (1 μM), respectively, when excited at 352 nm. Each fluorescence spectrum was measured at 20° C. in 50 mM sodium cacodylate (pH 7.2), 50 mM KCl and 0.1 mM EDTA. In (B), the solid line with solid circles, the wavy line with open circles and the solid line with crosses represent the fluorescence spectra of tRNA47s in the presence of 0 mM $Mg^{2+}$, 2 mM $Mg^{2+}$ and 5 mM $Mg^{2+}$, respectively. In (C), the solid line with solid circles, the wavy line with open circles and the solid line with crosses represent the fluorescence spectra of tRNA57s in the presence of 0 mM $Mg^{2+}$, 2 mM $Mg^{2+}$ and 5 mM $Mg^{2+}$, respectively.

The s base has two excitation maxima (at 299 and 352 nm). FIG. 7A shows the excitation and fluorescence spectra of s ribonucleoside (1 µM). As is apparent from FIG. 7A, s shows a fluorescence spectrum with its center at 434 nm, and the quantum yield of the fluorescence was 0.41 at pH 7.0. FIGS. 7B and 7C show the fluorescence spectra of tRNA 47s (1 µM) and tRNA 57s (1 µM), respectively, when excited at 352 nm. Each fluorescence spectrum was measured at 20° C. in 50 mM sodium cacodylate (pH 7.2), 50 mM KCl and 0.1 mM EDTA.

In this example, in a solution containing 50 mM sodium cacodylate and 50 mM KCl together with 0.1 mM EDTA or 2 mM or 5 mM $MgCl_2$ instead of EDTA, s (excited at 352 nm with a 3 nm spectral bandwidth) was measured for its fluorescence intensity at 434 nm and UV absorption at 260 nm to study the thermodynamic melting profiles of each tRNA transcript (1 µM).

Figure 8:
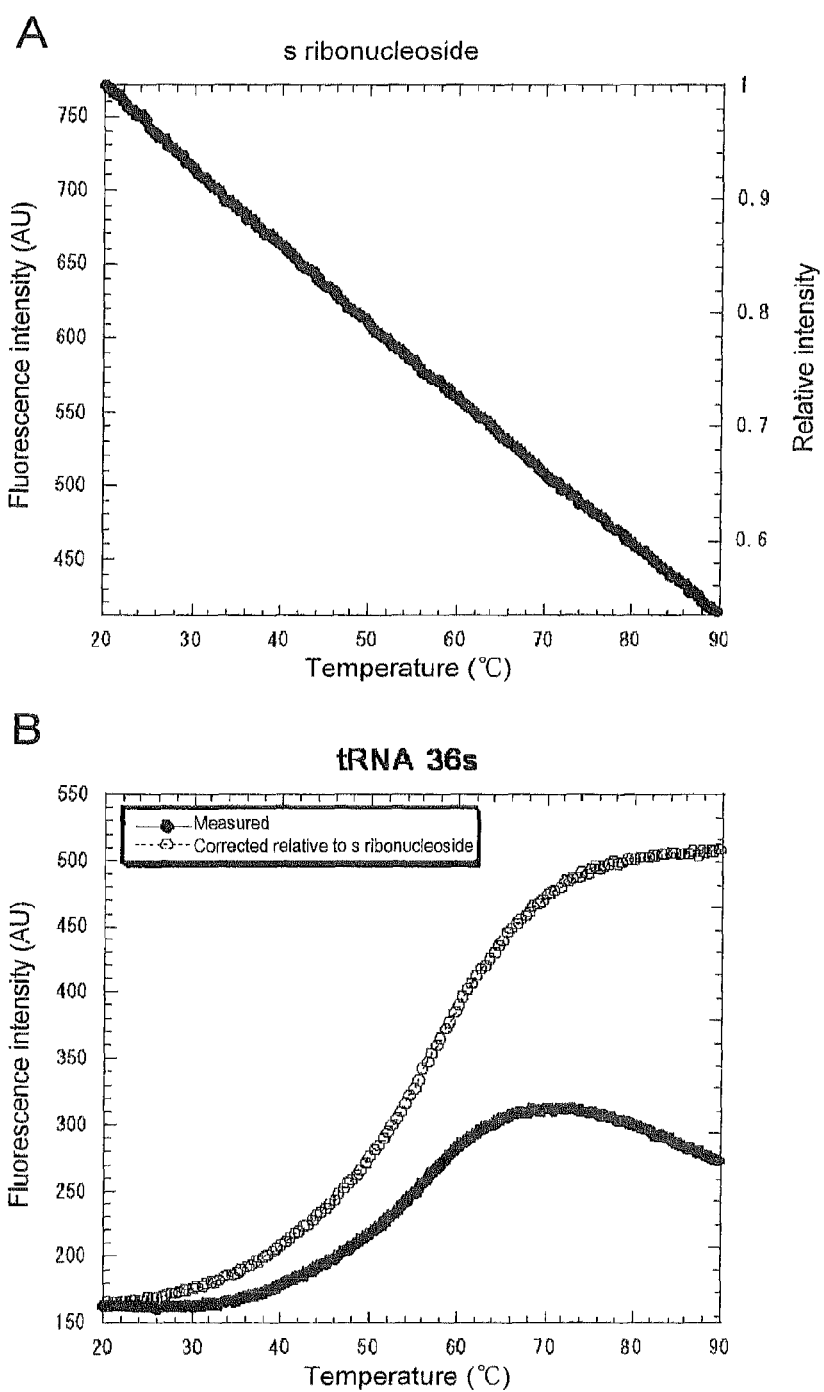
FIG. 8 shows (A) the temperature dependence of the fluorescence intensity of s ribonucleoside, and (B) an example showing the fluorescence intensity of tRNA 36s corrected relative to s ribonucleoside. The fluorescence intensity of each tRNA transcript was corrected according to the equation: Yct=Yt/(Rt/R20), wherein Yct represents the corrected intensity of each tRNA at t° C., Yt represents the measured fluorescence intensity of each tRNA at t° C., Rt represents the observed fluorescence intensity of s ribonucleoside at t° C., and R20 represents the observed fluorescence intensity of s ribonucleoside at 20° C.

Quenching of the s fluorescence by collision with solvent molecules is more likely to occur at a higher temperature (FIG. 8A). For this reason, temperature-dependent changes in the fluorescence intensity of each tRNA transcript were normalized by s nucleoside monomer. The melting temperature of each tRNA determined from temperature-dependent changes in its fluorescence intensity was calculated using IGOR Pro software (WaveMetrics. Inc.). More specifically, FIG. 8 shows (A) temperature-dependent changes in the fluorescence intensity of s ribonucleoside, and (B) the temperature dependence of the fluorescence intensity of tRNA 36s corrected in consideration of temperature-dependent changes in the fluorescence intensity of s ribonucleoside. The fluorescence intensity of each tRNA transcript was corrected according to the equation: Yct=Yt/(Rt/R20), wherein Yct represents the corrected intensity of each tRNA at t° C., Yt represents the fluorescence intensity of each tRNA actually measured at t° C., Rt represents the fluorescence intensity of s ribonucleoside at t° C., and R20 represents the fluorescence intensity of s ribonucleoside at 20° C.

3) Results

Figure 9:
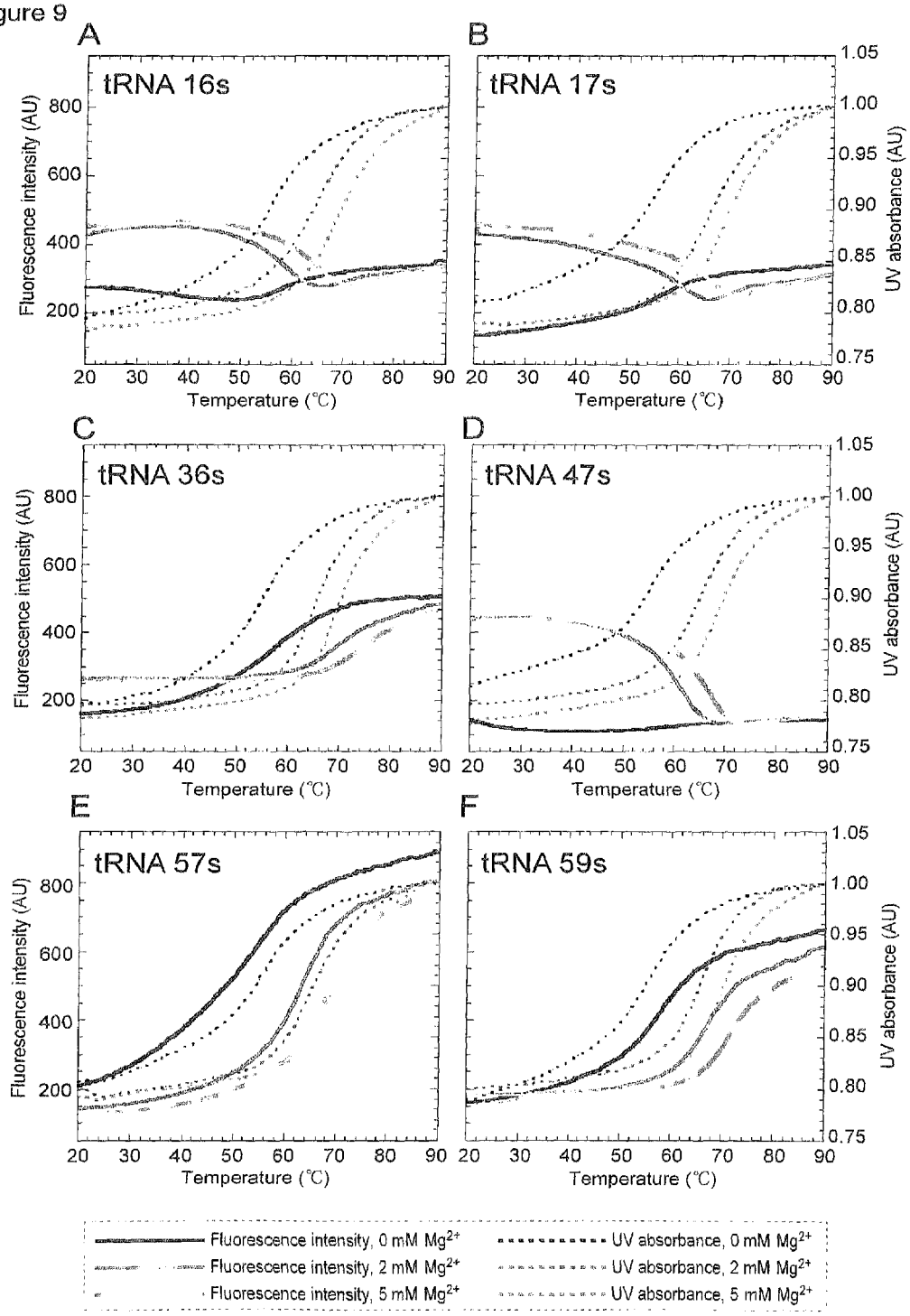
FIG. 9 shows the melting curves of tRNAs containing s at various positions, obtained from changes in their fluorescence intensity at 434 nm (solid lines) and obtained from changes in their UV absorption at 260 nm (wavy lines). The thick (black), middle (blue) and thin (red) solid lines represent melting curves obtained from changes in the fluorescence intensity at 434 nm in the presence of 0 mM $Mg^{2+}$, 2 mM $Mg^{2+}$ and 5 mM $Mg^{2+}$, respectively. The thick (black), middle (blue) and thin (red) wavy lines represent melting curves obtained from changes in the UV absorption at 260 nm in the presence of 0 mM $Mg^{2+}$, 2 mM $Mg^{2+}$ and 5 mM $Mg^{2+}$, respectively.

FIG. 9 shows the melting curves of 16s, 17s, 36s, 47s, 57s and 59s tRNAs obtained from temperature-dependent changes in their fluorescence intensity at 434 nm (solid lines) and obtained from changes in their UV absorption at 260 nm (wavy lines).

First, the UV melting temperature of each tRNA transcript containing s (64.6-66.4° C. in 2 mM $MgCl_2$) was as high as that of the natural tRNA transcript (65.5° C. in 2 mM $MgCl_2$). This suggests that the replacement of s at these positions does not significantly destabilize the tRNA structure.

Second, each tRNA containing s at a specific position showed characteristic fluorescence intensity changes reflecting the local structural features. The fluorescence properties of s in the presence of $Mg^{2+}$ (2 and 5 mM) are clearly divided into two groups: one includes tRNA 16s, 17s and 47s (Group 1), and the other includes tRNA 36s, 57s and 59s (Group 2). In the presence of 2 mM or 5 mM $Mg^{2+}$, the fluorescence intensity of s in Group 1 at low temperature was 1.7- to 3.4-fold larger than that of Group 2. This large fluorescence intensity of s in Group 1 decreased when the temperature increased, whereas the fluorescence intensity of in Group 2 increased with increase in temperature.

These results suggest that the s base at position 16, 17 or 47 is exposed to the solution at physiological temperature, and hence the non-specific interaction between s and other bases is increased upon denaturation of tRNA with increasing temperature. In contrast, the s base at position 36, 57 or 59 stacks at low temperature with its neighboring bases in tRNA folded into an L-shaped structure, and the tRNA is gradually denatured with increasing temperature to thereby break the stacking structure with the bases adjacent to s. Such a presumption is entirely consistent with the conformations of the original bases at each site in the L-shaped structure of tRNA, as analyzed by the X-ray crystal structure analysis (FIG. 4) (Non-patent Document 20). The fluorescence intensity of tRNA 16s, 17s and 47s is dramatically increased by addition of $Mg^{2+}$ at physiological temperature. This suggests that tRNA forms an L-shaped structure upon binding $Mg^{2+}$ to the tRNA, whereby the bases at these positions are exposed to the solution.

Third, the Tm values obtained from the fluorescent profiles reflect the stability of each local structure in the tRNA structure, in comparison with the Tm values obtained from the UV melting profiles. Table 3 shows melting temperatures (Tm) obtained from the fluorescent and UV profiles of yeast tRNA$^{Phe}$ containing s at a specific site.

Table 3: Melting temperatures (Tm) obtained from fluorescent and UV profiles of yeast tRNA$^{Phe}$ containing s at a specific site

TABLE 3

| | Tm (° C.) obtained from fluorescent profiles | | | Tm (° C.) obtained from UV profiles | | |
|---|---|---|---|---|---|---|
| | 0 mM $Mg^{2+}$ | 2 mM $Mg^{2+}$ | 5 mM $Mg^{2+}$ | 0 mM $Mg^{2+}$ | 2 mM $Mg^{2+}$ | 5 mM $Mg^{2+}$ |
| Original tRNA | — | — | — | 56.1 | 65.5 | 70.1 |
| tRNA 16s | n.c. | 58.0 | 64.0 | 55.6 | 64.6 | 69.1 |
| tRNA 17s | n.c. | 59.6 | 65.5 | 55.7 | 65.6 | 69.1 |
| tRNA 36s | 57.0 | 69.5 | 74.0 | 55.2 | 65.2 | 69.7 |
| tRNA 47s | n.c. | 61.1 | 66.0 | 55.3 | 65.2 | 68.8 |
| tRNA 57s | 54.5 | 63.6 | 68.5 | 55.8 | 65.1 | 69.6 |
| tRNA 59s | 58.1 | 67.1 | 71.5 | 55.8 | 66.4 | 70.3 |

The fluorescent and UV profiles were obtained by using each tRNA transcript (1 μM) in 50 mM sodium cacodylate (pH 7.2) and 50 mM KCl with or without $MgCl_2$. Each melting temperature was calculated using Igor Pro software (WaveMetrics. Inc.). n.c.: Not calculated.

By way of example, the Tm value obtained from the fluorescent profile of tRNA 36s (69.5° C. in 2 mM $MgCl_2$) was higher than that obtained from the UV profile (65.2° C. in 2 mM $MgCl_2$). This suggests that the anticodon stem-loop has a higher stability when compared to the stability of the entire tRNA structure. In contrast, the low stability of tRNA 16s (58.0° C. in 2 mM $MgCl_2$) and 17s (59.6° C. in 2 mM $MgCl_2$) suggests that the partial structure including the D-loop may be a fragile region within the tRNA structure.

Example 4

FRET Experiment on RNA Strands Incorporating Artificial Bases a and FAM-y

The use of s-Pa base pairing during transcription allows efficient introduction of a fluorescent artificial base s into RNA. When this s-Pa base pair is combined with the v-y base pair previously developed by the inventors of the present invention, both s and y or both s and 5-modified y can be introduced into a single strand of RNA at any positions. In particular, the use of y introduced with FAM allows the observation of FRET between s and FAM-y.

In this example, template DNAs for transcription containing Pa and v at various sites were chemically synthesized, and transcription was effected using these templates and the respective substrates of s and y or FAM-y (sTP, yTP, FAM-yTP).

T7 RNA Polymerase-Mediated Transcription Reaction (Analysis of RNA 39-Mer Site-Specifically Incorporating Both s and y)

Double-stranded template DNA (5 μM) was annealed in 10 mM Tris-HCl buffer (pH 7.6) containing 10 mM NaCl (temperature conditions: heating at 95° C. for 3 minutes, followed by slow cooling to 4° C. at a rate of –0.1° C./second). T7 transcription reaction was accomplished in a reaction solution (20 μl in total) containing 40 mM Tris-HCl buffer (pH 8.0), 8 mM $MgCl_2$, 2 mM spermidine, 5 mM DTT, 0.01% Triton X-100, 2 μCi [γ-$^{32}$P]GTP, 1 mM NTPs, 0-1 mM sTP, 0-1 mM yTP, 0.5 μM template DNA, and 50 units of T7 RNA polymerase (Takara). After reaction at 37° C. for 3 hours, an electrophoresis dye solution containing 10 M urea was added in an equal volume (20 μl) to stop the reaction. This solution was heated at 75° C. for 3 minutes and then electrophoresed on a 15% polyacrylamide-7 M urea gel. The transcripts were analyzed with a bio-imaging analyzer (FIG. 10).

Figure 11:
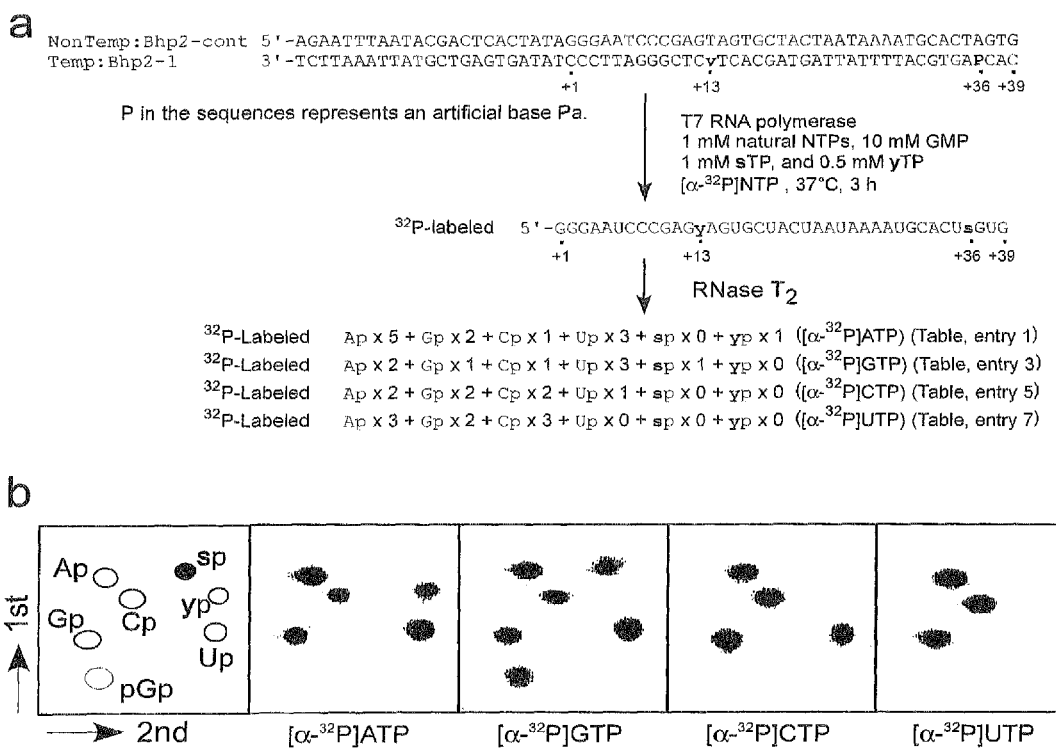
FIG. 11 shows the results of nucleotide composition analysis on the transcripts (Bhp2-1) prepared through transcription using v-y and s-Pa base pairing. Quantification of each spot in FIG. 11b is summarized in Table 4.

Nucleotide Composition Analysis for Products of T7 RNA Polymerase-mediated Transcription Reaction T7 RNA polymerase-mediated transcription reaction was accomplished in a reaction solution containing 40 mM Tris-HCl buffer (pH 8.0), 8 mM $MgCl_2$, 2 mM spermidine, 5 mM DTT, 0.01% Triton X-100, 2 μCi [α-$^{32}$P]ATP or 2 μCi [α-$^{32}$P]GTP or 2 μCi [α-$^{32}$P]CTP or 2 μCi [α-$^{32}$P]UTP, 1 mM NTPs, 0-1 mM sTP, 0-1 mM yTP, 0.5 μM template DNA, and 50 units of T7 RNA polymerase (Takara). The transcript was purified by electrophoresis on a 15% polyacrylamide-7 M urea gel, eluted from the gel and then collected by ethanol precipitation in the presence of tRNA (0.05 OD). This sample was dissolved in 10 μl sterilized water, and the resulting solution (8.5 μl) was provided for complete digestion with RNase $T_2$. To the solution (8.5 μl), RNase $T_2$ (1.5 μl, 0.5 U/μl) was added and reacted at 37° C. for 2 hours. A part of this solution was spotted on a TLC plate (Merck, 10 cm×10 cm) and developed two-dimensionally. The developing solutions used for the first and second dimensions were isobutyric acid:concentrated aqueous ammonia:water=66:1:33 (v/v/v) and 2-propanol:hydrochloric acid:water=65:10:25 (v/v/v), respectively. The developed spots were detected and analyzed with a bio-imaging analyzer (FIG. 11, Table 4).

T7 RNA Polymerase-mediated Transcription Reaction (Preparation of RNA 39-mer Site-Specifically Incorporating Both s and y or Both s and FAM-y)

T7 transcription reaction was accomplished in a reaction solution (50 μl in total) containing 40 mM Tris-HCl buffer (pH 8.0), 8 mM $MgCl_2$, 2 mM spermidine, 5 mM DTT, 0.01% Triton X-100, 1 mM NTPs, 1 mM sTP, 1 mM yTP or 1 mM FAM-yTP, 0.5 μM template DNA, and 125 units of T7 RNA polymerase (Takara). After reaction at 37° C. for 6 hours, a DNase I solution was added and incubated at 37° C. for 15 minutes to digest the template DNA. After an electrophoresis dye solution containing 10 M urea was added in an equal volume (50 µl) to stop the reaction, the reaction solution was heated at 75° C. for 3 minutes and then electrophoresed on a 15% polyacrylamide-7 M urea gel to purify the desired transcript 39-mer. After elution with sterilized water from the gel, the transcript was collected by ethanol precipitation and measured for UV absorption to determine the concentration of the desired transcript RNA 39-mer.

Fluorescence Spectrum Measurement

The RNA 39-mer site-specifically incorporating both s and y or both s and FAM-y (0.2 KM) was used to measure a fluorescence spectrum at 20° C. in 10 mM sodium phosphate buffer (pH 7.0), 100 mM NaCl and 0.1 mM EDTA. In the annealing operation for the RNA sample before measurement, a solution containing the RNA 39-mer (0.2 µM) as well as a solution containing the RNA 39-mer and a complementary RNA 42-mer (0.4 µM) having a sequence complementary to the 39-mer were each heated at 75° C. for 3 minutes and then slowly cooled to 4° C. at a rate of −0.1° C./3 seconds. The annealed samples were stored at 4° C. For use in measurement, each sample was transferred to a measuring cell and allowed to stand at 20° C. for 2 minutes or longer, followed by starting spectral scanning (360-650 nm). For fluorimetry (excitation wavelength: 350 nm), a 3×3 mm cell was used, and the following settings were used to measure each spectrum: response 0.5 s, scanning speed 2000 nm/minute, sensitivity fixed at PMT 500V in manual mode, and slit bandwidth fixed at 5 nm (FIG. 12).

Results

FIG. 10 shows strategies for site-specific introduction of y and s into RNA through transcription using v-y and s-Pa base pairing, along with the results of polyacrylamide electrophoresis on the transcripts.

In more detail, FIG. 10a shows the sequences of template DNAs and conditions for transcription reaction (in the sequences, Pa is represented by P). The transcripts (Bhp2-1, Bhp2-2, Bhp2-3) were studied by polyacrylamide gel electrophoresis (FIG. 10b), indicating that transcription in the presence of both sTP and yTP resulted in higher amounts of the transcripts. In turn, to study whether s and y were selectively incorporated into RNA, substrates having radioactive phosphorus introduced at the α-position, i.e., [α-$^{32}$P]ATP, [α-$^{32}$P]GTP, [α-$^{32}$P]CTP and [α-$^{32}$P]UTP were each used separately for transcription, and the radioactively labeled transcripts were hydrolyzed with RNase T$_2$ into nucleoside 3'-monophosphates, followed by two-dimensional TLC to analyze nucleoside 3'-monophosphates whose phosphoric acid was radioactively labeled, thereby examining the nucleotide composition of the transcripts (FIG. 11).

In this technique, upon incorporation of a radioactive substrate, a nucleotide located at the 5'-side of the substrate can be detected on two-dimensional TLC. For example, FIG. 11b shows the results of two-dimensional TLC on Bhp2-1. In Bhp2-1, y is located at the 5'-side of A and s is located at the 5'-side of G. If y and s are selectively incorporated into RNA opposite v and Pa in the template, respectively, a spot corresponding to yp (i.e., nucleoside 3'-monophosphate of y) will appear on two-dimensional TLC of the transcript labeled with [α-$^{32}$P]ATP, while a spot corresponding to sp (i.e., nucleoside 3'-monophosphate of s) will appear in the case of the transcript labeled with [α-$^{32}$P]GTP. In FIG. 11b, the intended spot actually appears on each TLC. Moreover, the transcript labeled with [α-$^{32}$P]CTP or [α-$^{32}$P]UTP shows no spot corresponding to either yp or sp, indicating that none of these artificial bases is misincorporated opposite natural bases in the template. Further, each spot on two-dimensional TLC was quantified; the results obtained are summarized in Table 4.

TABLE 4

Nucleotide composition analysis of RNA (Bhp2-1) incorporating s and y

| Entry No. | Template | [α-$^{32}$P] NTP | yTP (mM) | sTP (mM) | Composition of nucleotides incorporated as 5' neighbor of A or G or C or U$^a$ | | | | | |
|---|---|---|---|---|---|---|---|---|---|---|
| | | | | | Ap | Gp | Cp | Up | sp | yp |
| 1 | 2-1 | ATP | 0.5 | 1 | 4.90$^b$ [5]$^c$ (0.03)$^d$ | 2.01 [2] (0.03) | 1.01 [1] (0.01) | 3.03 [3] (0.04) | 0.03 [0] (0.02) | 1.01 [1] (0.02) |
| 2 | 2-1 | ATP | 1 | 1 | 4.94 [5] (0.06) | 2.00 [2] (0.02) | 1.01 [1] (0.02) | 2.96 [3] (0.05) | 0.03 [0] (0.01) | 1.05 [1] (0.01) |
| 3 | 2-1 | GTP | 0.5 | 1 | 2.05 [2] (0.02) | 1.03 [1] (0.02) | 1.01 [1] (0.01) | 2.95 [3] (0.02) | 0.92 [1] (0.02) | 0.03 [0] (0.01) |
| 4 | 2-1 | GTP | 1 | 1 | 2.00 [2] (0.02) | 1.05 [1] (0.04) | 1.01 [1] (0.01) | 2.95 [3] (0.03) | 0.92 [1] (0.03) | 0.06 [0] (0.01) |
| 5 | 2-1 | CTP | 0.5 | 1 | 1.95 [2] (0.02) | 1.99 [2] (0.03) | 1.94 [2] (0.02) | 1.06 [1] (0.02) | 0.05 [0] (0.01) | 0.01 [0] (<0.01) |
| 6 | 2-1 | CTP | 1 | 1 | 1.94 [2] (0.01) | 2.01 [2] (0.05) | 1.95 [2] (0.01) | 1.05 [1] (0.03) | 0.04 [0] (0.02) | 0.01 [0] (<0.01) |
| 7 | 2-1 | UTP | 0.5 | 1 | 3.02 [3] (0.06) | 1.94 [2] (0.05) | 3.00 [3] (0.01) | 0.02 [0] (0.01) | 0.02 [0] (0.01) | n.d.$^e$ [0] (—) |
| 8 | 2-1 | UTP | 1 | 1 | 3.05 [3] (0.05) | 1.90 [2] (0.09) | 3.01 [3] (0.06) | 0.02 [0] (<0.01) | 0.02 [0] (0.01) | n.d. [0] (—) |
| 9 | cont | ATP | 0.5 | 1 | 4.94 [5] (0.06) | 2.05 [2] (0.06) | 1.01 [1] (0.03) | 4.90 [5] (0.05) | 0.02 [0] (0.01) | 0.07 [0] (0.03) |
| 10 | cont | ATP | 1 | 1 | 4.94 [5] (0.03) | 2.05 [2] (0.02) | 1.05 [1] (0.02) | 4.79 [5] (0.05) | 0.02 [0] (0.01) | 0.15 [0] (0.01) |
| 11 | cont | ATP | 0 | 0 | 4.95 [5] (0.03) | 2.03 [2] (0.01) | 1.03 [1] (0.01) | 4.99 [5] (0.05) | n.d. [—] (—) | n.d. [—] (—) |
| 12 | cont | GTP | 0.5 | 1 | 2.97 [3] (0.06) | 1.05 [1] (0.03) | 1.01 [1] (0.01) | 2.92 [3] (0.04) | 0.01 [0] (<0.01) | 0.03 [0] (<0.01) |
| 13 | cont | GTP | 1 | 1 | 2.97 [3] (0.03) | 1.05 [1] (0.01) | 1.03 [1] (0.02) | 2.89 [3] (0.03) | 0.01 [0] (<0.01) | 0.06 [0] (<0.01) |

TABLE 4-continued

Nucleotide composition analysis of RNA (Bhp2-1) incorporating s and y

| Entry No. | Template | [α-$^{32}$P] NTP | yTP (mM) | sTP (mM) | Composition of nucleotides incorporated as 5' neighbor of A or G or C or U[a] | | | | | |
|---|---|---|---|---|---|---|---|---|---|---|
| | | | | | Ap | Gp | Cp | Up | sp | yp |
| 14 | cont | GTP | 0 | 0 | 2.98 [3] (0.04) | 1.04 [1] (0.01) | 1.02 [1] (0.01) | 2.96 [3] (0.04) | n.d. [—] (—) | n.d. [—] (—) |

[a]Composition of nucleotides incorporated at 5'-neighbor of A (Entry Nos. 1, 2 and 9-11), G (Entry Nos. 3, 4 and 12-14), C (Entry Nos. 5 and 6) or U (Entry Nos. 7 and 8) shown in FIG. 11
[b]The values were determined by using the following equation. (Radioactivity of each nucleotide)/[All nucleotides (3'-monophosphates)] × (Total number of nucleotides at 5'-neighbor of [α-$^{32}$P]NTP]
[c]The theoretical number of each nucleotide is shown in square brackets.
[d]The standard deviation is shown in parentheses.
[e]Not detected The results are shown for the cases where yTP was used in an amount of 0.5 mM or 1 mM during transcription. The results of Entry Nos. 1-8 are all well consistent with the theoretical values (the numerical values in brackets). In Entry Nos. 9-14, which show the results obtained for using template DNA composed only of natural bases, Entry No. 10 indicated that a slight amount of yp was incorporated opposite natural template bases when using 1 mM yTP. Thus, it is preferable to set the amount of yTP used during transcription to 0.5 mM. These results indicate that when transcription is effected using s-Pa base paring in combination with v-y base pairing, it is possible to selectively introduce s and y into a single strand of RNA.

For further study, the substrate of y was replaced by a substrate modified to have FAM at the 5-position of y (FAM-yTP). This substrate and sTP were used for transcription of Bhp2-1, and the transcript was purified by gel electrophoresis and studied for its fluorescence properties. Bhp2-1 alone forms a hairpin structure, in which s and FAM-y are located at positions allowing base pairing, whereby FRET will be observed between s and FAM-y. Upon addition of a complementary strand of this RNA, a double-stranded structure is formed to give a distance between s and FAM-y, thereby reducing the efficiency of FRET. The fluorescence spectrum obtained for RNA of this double-stranded structure is shown in FIG. 12b, while the fluorescence spectrum obtained for the hairpin-type RNA is shown in FIG. 12c (solid lines). Each fluorescence spectrum is compared to the spectrum obtained for RNA incorporating s and y (broken line: this RNA shows no FRET event and hence serves as a control showing the fluorescence spectrum of s). When s was excited at 350 nm, FRET was observed and the fluorescence from FAM-y appeared around 521 nm in both cases. However, the hairpin-type RNA shows a stronger fluorescence intensity of FAM-y and also causes significant quenching of s over the control (broken line).

This result indicated that FRET was observed in correlation with the distance between s and FAM-y. Thus, when s and FAM-y are introduced at various sites in RNA and measured for the efficiency of FRET between them, the distance between s and FAM-y can be estimated and is helpful in RNA structural analysis. Although conventional analyses such as X-ray crystal structure analysis and NMR structural analysis provided only information about static RNA structures, the technique used in this example makes it possible to know the dynamics of conformational changes in RNA in a solution.

Example 5

Figure 13:
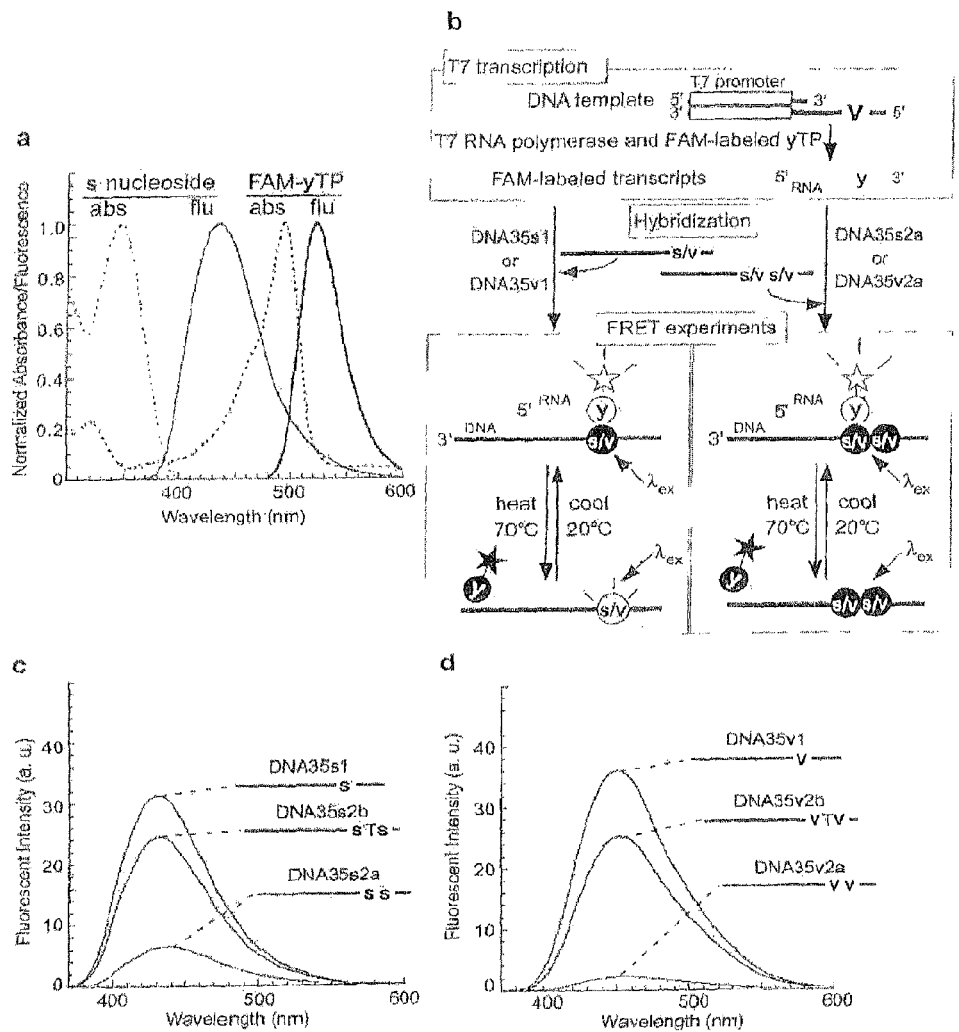
FIG. 13a shows the fluorescence (flu, solid line) and absorption (abs, broken line) spectra of s deoxyribonucleoside (thin line) and FAM-yTP (thick line) in phosphate buffer (pH 7.0).
FIG. 13b shows a scheme for FRET experiment. Solid circles and open circles represent their low fluorescence state and their high fluorescence state, respectively, when unnatural base s or v was excited ($\lambda_{ex}$).
FIGS. 13c and 13d show the steady-state fluorescence emission spectra of single-stranded DNAs containing s base(s) (c: DNA35s1, DNA35s2a and DNA35s2b) and single-stranded DNAs containing v base(s) (c: DNA35v1, DNA35v2a and DNA35v2b).

FRET Experiment on Artificial Base Pairing Between s or v and FAM-y in Nucleic Acid Duplexes In DNA/RNA duplexes, the FRET experiment was performed between a fluorescent artificial base 2-amino-6-(2-thienyl)purin-9-yl or 2-amino-6-(thiazolyl)purin-9-yl group (hereinafter referred to as s or v, respectively) and a fluorophore-labeled 2-oxo-(1H)pyridin-3-yl group (hereinafter referred to as y). The emission spectrum of s or v overlapped with the absorption spectrum of a nucleotide derivative which was FAM-labeled 5-(3-amino-1-propynyl)-y (FAM-yTP) or FAM-labeled 5-[3-(6-aminohexanamido)-1-propynyl]-y (FAM-hx-yTP) (FIG. 13a). Thus, s or v in DNA fragments serves as a fluorescent donor, while FAM-y or FAM-hx-y in their complementary RNA fragments serves as a fluorescent acceptor.

Synthesis of DNA Containing an Artificial Base s or v

DNA containing an artificial base s or v was synthesized as described, for example, in WO 01/05801 or WO 2005/026187 by using a cyanoethylphosphoroamidite derivative of a nucleotide containing an artificial base s or v in accordance with the DNA chemical synthesis method well known in the art. The sequence of the chemically synthesized 35-mer DNA is as follows: 5'-CAN$_1$N$_2$N$_3$CTCGGGATTCCCTATAGTGAGT CGTATTAT-3' (SEQ ID NO: 20; DNA in which N$_1$N$_2$N$_3$ is CTs or CTv is referred to as DNA35s1 or DNA35v1, respectively; DNA in which N$_1$N$_2$N$_3$ is Css or Cvv is referred to as DNA35s2a or DNA35v2a, respectively; and DNA in which N$_1$N$_2$N$_3$ is sTs or vTv is referred to as DNA35s2b or DNA35v2b, respectively). The resulting DNA was purified by gel electrophoresis.

Preparation of RNA Incorporating FAM-y or FAM-hx-y 17-mer RNA incorporating FAM-y or FAM-hx-y at the N' position (5'-GGGAAUCCCGAGN'AGUG-3'; SEQ ID NO: 21) was prepared through T7 transcription using T7 RNA polymerase and a substrate of FAM-y or FAM-hx-y (FAM-yTP or FAM-hx-yTP). The template (composed of DNA35v1 as a coding strand and 5'-ATAATACGACTCACTATAGGG-3' (SEQ ID NO: 22) as a non-coding strand, 10 μM each) was annealed in a buffer solution containing 10 mM Tris-HCl (pH 7.6) and 10 mM NaCl by heating at 95° C. and then slow cooling to 4° C. Transcription reaction was accomplished in a buffer solution containing 40 mM Tris-HCl (pH 8.0), 24 mM MgCl$_2$, 2 mM spermidine, 5 mM DTT and 0.01% Triton X-100, in the presence of 1 mM natural NTPs, 1 mM FAM-yTP or FAM-hx-yTP, 2 μM template and 2.5 units/μL T7 RNA polymerase (Takara). After incubation at 37° C. for 3 hours, a dye solution containing 10 M urea and 0.05% BPB was added in an equal volume to stop the reaction. The reaction mixture was heated at 75° C. for 3 minutes and the 17-mer transcript was purified by gel electrophoresis.

Fluorescence Spectrum Measurement

Fluorescence spectra were measured in a buffer containing 10 mM sodium phosphate (pH 7.0), 100 mM NaCl and 0.1 mM EDTA. Emission spectra were recorded with an excitation wavelength of 350 nm for s and 360 nm for v, respectively. The emission spectral bandpass was set to 5 nm.

The 17-mer RNA site-specifically incorporating FAM-y or FAM-hx-y was hybridized with 35-mer DNA site-specifically containing one or two s or v bases (DNA35s1, 35s2a, 35S2b, 35v1, 35v2a or 35v2b) to measure emission spectra for the DNA/RNA duplex at different temperatures (20° C. and 70° C.).

Results

Figure 14:
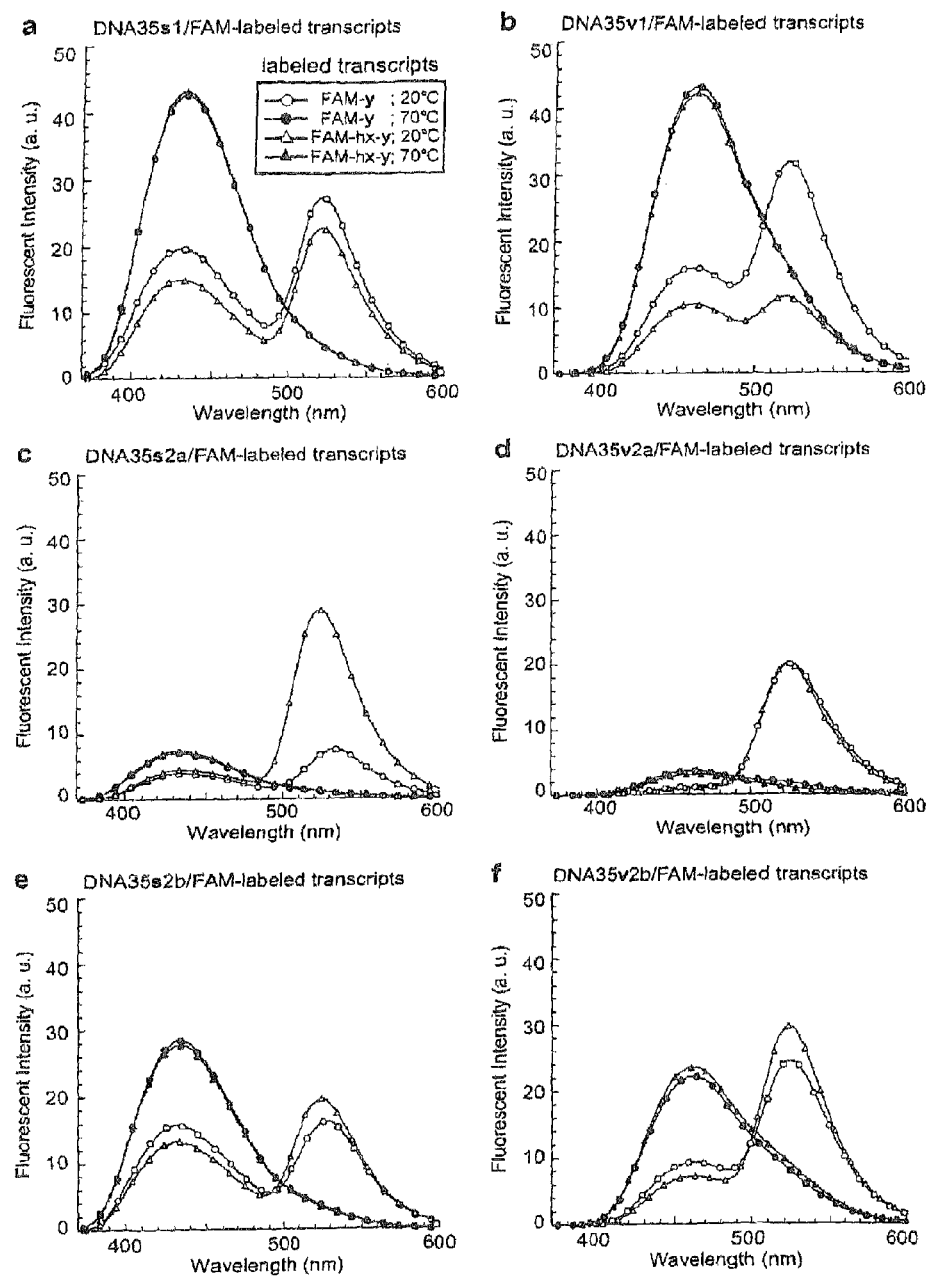
FIG. 14 shows the steady-state fluorescence emission spectra of DNA/RNA duplexes. 35-mer DNAs (a: DNA35s1; b: DNA35v1; c: DNA35s2a; d: DNA35v2a; e: DNA35s2b; and f: DNA35v2b) were each hybridized with 17-mer RNA containing FAM-y (open circles and solid circles) or FAM-hx-y (open triangles or solid triangles). The open circles and open triangles represent the spectra at 20° C., while the solid circles and solid triangles represent the spectra at 70° C.

Resonance energy transfer was observed between a low fluorescence state of s or v and a high fluorescence state of FAM-y or FAM-hx-y. FRET occurred when DNA35s1 or DNA35v1 formed a duplex at 20° C. with the 17-mer RNA site-specifically incorporating FAM-y or FAM-hx-y, whereas FRET was significantly reduced when the duplex was denatured at 70° C. (FIGS. 14a and 14b). In addition, FRET occurred efficiently in a duplex formed between DNA35s2a or DNA35v2a and the RNA site-specifically incorporating FAM-y or FAM-hx-y (FIGS. 14c and 14d).

Interestingly, the fluorescence intensity of single-stranded DNA35s2a or DNA35v2a containing two adjacent artificial bases was significantly decreased, whereas there was no significant decrease in the fluorescence intensity of single-stranded DNA35s2b or DNA35v2b containing two artificial bases partitioned by one T base (FIGS. 13c and 13d). Such a decrease observed in the fluorescence intensity of single-stranded DNA35s2a or DNA35v2a is caused by self-quenching between two adjacent artificial bases.

Figure 15:
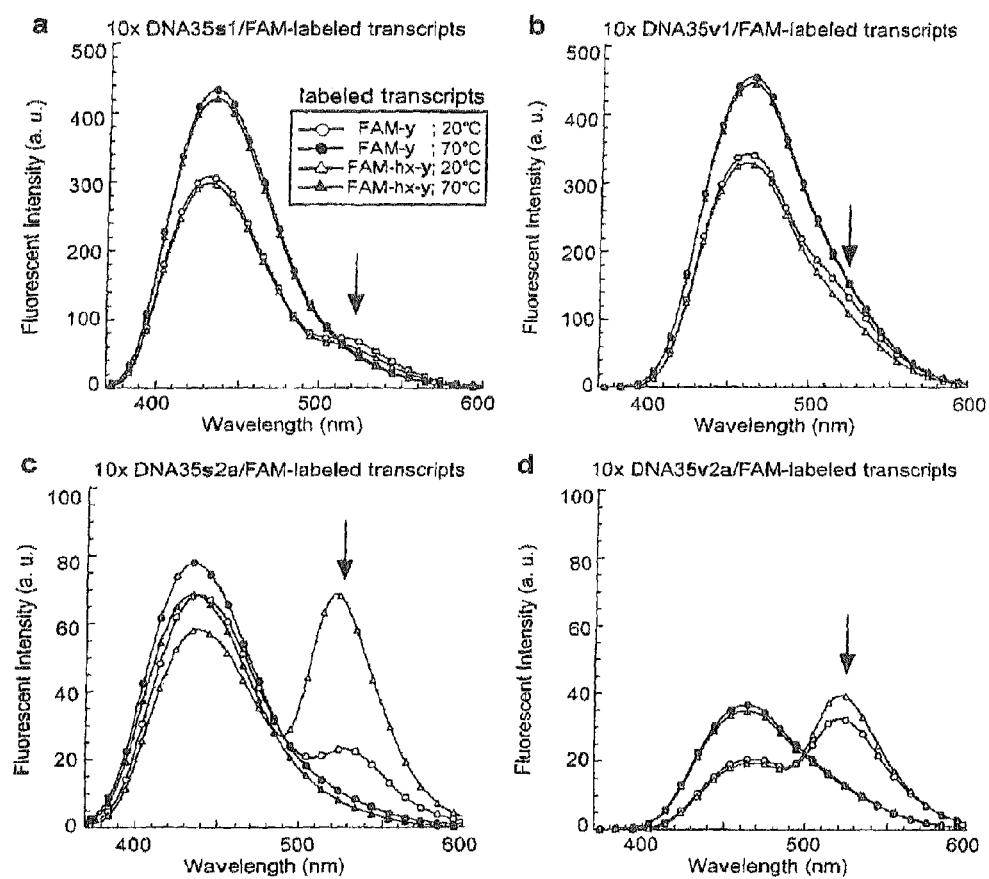
FIG. 15 shows the steady-state fluorescence emission spectra of DNA/RNA duplexes when using excessive DNA probes containing artificial bases. 35-mer DNAs (1 µM) (a: DNA35s1; b: DNA35v1; c: DNA35s2a; and d: DNA35v2a) were each hybridized with 17-mer RNA (100 nM) containing FAM-y (open circles and solid circles) or FAM-hx-y (open triangles and solid circles). The open circles and open triangles represent the spectra at 20° C., while the solid circles and solid triangles represent the spectra at 70° C.

Since a strong FAM fluorescence from the 17-mer RNA was also observed during formation of a duplex with DNA35s2a or DNA35v2a in which self-quenching occurred between two adjacent artificial bases, this FRET system using a self-quenched probe facilitates the use of excessive probe against a target strand. When 10 molar equivalents of DNA35s1 or DNA35v1 containing one artificial base was used against the 17-mer RNA, resonance energy transfer was completely buried in the background fluorescence of DNA35s1 or DNA35v1 (FIGS. 15a and 15b). In contrast, when 10 molar equivalents of DNA35s2a or DNA35v2a containing two adjacent artificial bases was used against the 17-mer RNA, FRET was clearly observed between ss- or vv-containing DNA and FAM-containing RNA (FIGS. 15c and 15d). Thus, such a FRET system using a self-quenched probe containing two adjacent artificial bases allows observation of a FRET phenomenon while reducing the background of a fluorescent donor, and hence enables the detection of complementary strands containing a fluorescent acceptor even in the presence of excessive donor probe. Moreover, since excessive self-quenched DNA probe facilitates the formation of a duplex with its complementary fluorescent acceptor strand, the FRET efficiency can be increased.

The invention claimed is:

1. A nucleic acid, in which a nucleotide having a substituted or unsubstituted 2-formyl-1H-pyrrol-1-yl group as a base forms a base pair with a nucleotide having a 6-substituted 9H-purin-9-yl group as a base wherein the substituted or unsubstituted 2-formyl-1H-pyrrol-1-yl group is selected from the group consisting of:
   A1) a 2-formyl-1H-pyrrol-1-yl group;
   A2) a 2-formyl-4-(1-propyn-1-yl)-1H-pyrrol-1-yl group;
   A3) a 2-formyl-4-methyl-1H-pyrrol-1-yl group; and
   A4) a 2-formyl-4-ethynyl-1H-pyrrol-1-yl group, and the 6-substituted 9H-purin-9-yl group is selected from the group consisting of:
   B1) a 2-amino-6-(2-thienyl)-9H-purin-9-yl group;
   B2) a 6-(2-thienyl)-9H-purin-9-yl group;
   B3) a 2-amino-6-(4-methyl-2-thienyl)-9H-purin-9-yl group;
   B4) a 6-(4-methyl-2-thienyl)-9H-purin-9-yl group;
   B5) a 2-amino-6-(5-methyl-2-thienyl)-9H-purin-9-yl group;
   B6) a 6-(5-methyl-2-thienyl)-9H-purin-9-yl group;
   B7) a 2-amino-6-(2-thiazolyl)-9H-purin-9-yl group;
   B8) a 6-(2-thiazolyl)-9H-purin-9-yl group;
   B9) a 2-amino-6-(4-methyl-2-thiazolyl)-9H-purin-9-yl group;
   B10) a 6-(4-methyl-2-thiazolyl)-9H-purin-9-yl group;
   B11) a 2-amino-6-(5-methyl-2-thiazolyl)-9H-purin-9-yl group; and
   B12) a 6-(5-methyl-2-thiazolyl)-9H-purin-9-yl group.

2. The nucleic acid according to claim 1, wherein the substituted or unsubstituted 2-formyl-1H-pyrrol-1-yl group is a 2-formyl-1H-pyrrol-1-yl group, and the 6-substituted 9H-purin-9-yl group is a 2-amino-6-(2-thienyl)-9H-purin-9-yl group.

3. The nucleic acid according to claim 1, which forms a base pair(s) in the step of transcription, reverse transcription, replication or translation.

4. The nucleic acid according to claim 1, wherein the nucleotide having a substituted or unsubstituted 2-formyl-1H-pyrrol-1-yl group as a base is a part of DNA, and the nucleotide having a 6-substituted 9H-purin-9-yl group as a base is a part of RNA.

5. A method for prepairing a nucleic acid incorporating a nucleotide having a 6-substituted 9H-purin-9-yl group as a base, which comprises:
   effecting transcription, reverse transcription or replication by using, as a template, a nucleic acid incorporating a nucleotide having a substituted or unsubstituted 2-formyl-1H-pyrrol-1-yl group as a base, so that the nucleotide having a 6-substituted 9H-purin-9-yl group is incorporated at a site complementary to the nucleotide having a substituted or unsubstituted 2-formyl-1H-pyrrol-1-yl group,
   wherein the substituted or unsubstituted 2-formyl-1H-pyrrol-1-yl group is selected from the group consisting of:
   A1) a 2-formyl-1H-pyrrol-1-yl group;
   A2) a 2-formyl-4-(1-propyn-1-yl)-1H-pyrrol-1-yl group;
   A3) a 2-formyl-4-methyl-1H-pyrrol-1-yl group; and
   A4) a 2-formyl-4-ethynyl-1H-pyrrol-1-yl group, and the 6-substituted 9H-purin-9-yl group is selected from the group consisting of:
   B1) a 2-amino-6-(2-thienyl)-9H-purin-9-yl group;
   B2) a 6-(2-thienyl)-9H-purin-9-yl group;
   B3) a 2-amino-6-(4-methyl-2-thienyl)-9H-purin-9-yl group;
   B4) a 6-(4-methyl-2-thienyl)-9H-purin-9-yl group;
   B5) a 2-amino-6-(5-methyl-2-thienyl)-9H-purin-9-yl group;
   B6) a 6-(5-methyl-2-thienyl)-9H-purin-9-yl group;
   B7) a 2-amino-6-(2-thiazolyl)-9H-purin-9-yl group;
   B8) a 6-(2-thiazolyl)-9H-purin-9-yl group;
   B9) a 2-amino-6-(4-methyl-2-thiazolyl)-9H-purin-9-yl group;
   B10) a 6-(4-methyl-2-thiazolyl)-9H-purin-9-yl group;
   B11) a 2-amino-6-(5-methyl-2-thiazolyl)-9H-purin-9-yl group; and
   B12) a 6-(5-methyl-2-thiazolyl)-9H-purin-9-yl group.

6. The method according to claim 5, wherein the template has two or more nucleotides having a substituted or unsubstituted 2-formyl-1H-pyrrol-1-yl group as a base.

7. A nucleic acid incorporating a nucleotide having a 6-substituted 9H-purin-9-yl group as a base, which is prepared by the method according to claim 5.

8. The nucleic acid according to claim 7, which is tRNA, mRNA, antisense DNA or RNA, a ribozyme, an aptamer or siRNA, 9. A method for analyzing the stereostructure of a local region in the nucleic acid according to claim 7, which comprises measuring a temperature- and/or ion concentration-induced change in the fluorescence intensity from the base in the nucleotide having a 6-substituted 9H-purin-9-yl group as a base, wherein the local region includes the nucleotide.

10. The method according to claim 9, in which a determination is made that the nucleotide having a 6-substituted 9H-purin-9-yl group as a base stacks with its conformationally neighboring nucleotides at in vivo temperature if the fluorescence intensity from the base in the nucleotide is substantially increased with increase in temperature, or alternatively, a determination is made that the nucleotide is exposed outside at in vivo temperature if the fluorescence intensity is substantially decreased or not increased with increase in temperature.

11. A method for detecting the formation of a nucleic acid duplex, which comprise:
I) inducing hybridization between the following nucleic acids:
    i) a nucleic acid incorporating a nucleotide having a 6-substituted 9H-purin-9-yl group as a base, which is prepared by the method according to claim 5, and
    ii) a nucleic acid incorporating a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX); and
II) measuring a change in the fluorescence spectrum.)

12. The method according to claim 11, wherein the 6-substituted 9H-purin-9-yl group in I)i) is selected from the group consisting of:
B1) a 2-amino-6-(2-thienyl)-9H-purin-9-yl group;
B2) a 6-(2-thienyl)-9H-purin-9-yl group;
B3) a 2-amino-6-(4-methyl-2-thienyl)-9H-purin-9-yl group;
B4) a 6-(4-methyl-2-thienyl)-9H-purin-9-yl group;
B5) a 2-amino-6-(5-methyl-2-thienyl)-9H-purin-9-yl group;
B6) a 6-(5-methyl-2-thienyl)-9H-purin-9-yl group;
B7) a 2-amino-6-(2-thiazolyl)-9H-purin-9-yl group;
B8) a 6-(2-thiazolyl)-9H-purin-9-yl group;
B9) a 2-amino-6-(4-methyl-2-thiazolyl)-9H-purin-9-yl group;
B10) a 6-(4-methyl-2-thiazolyl)-9H-purin-9-yl group;
B11) a 2-amino-6-(5-methyl-2-thiazolyl)-9H-purin-9-yl group; and
B12) a 6-(5-methyl-2-thiazolyl)-9H-purin-9-yl group.

13. The method according to claim 11, wherein the nucleic acid in I)ii) is a nucleic acid incorporating a nucleotide having a 5-substituted-2-oxo(1H)pyridin-3-yl group as a base, whose 5-position is attached either directly or through a linker to 5-carboxyfluorescein (5-FAM) or 6-carboxyfluorescein (6-FAM).

14. A method for preparing a nucleic acid incorporating the following nucleotides on the same strand:
    i) a nucleotide having a 6-substituted 9H-purin-9-yl group as a base; and
    ii) a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX),
    wherein the method comprises effecting transcription, reverse transcription or replication by using, as a template, a nucleic acid incorporating the following nucleotides:
    iii) a nucleotide having a substituted or unsubstituted 2-formyl-1H-pyrrol-1-yl group as a base; and
    iv) a nucleotide having a 6-substituted 9H-purin-9-yl group as a base,
    so that the nucleotide of i) is incorporated at a site complementary to the nucleotide of iii), while the nucleotide of ii) is incorporated at a site complementary to the nucleotide of iv).

15. A nucleic acid incorporating the following nucleotides on the same strand, which is prepared by the method according to claim 14:
    i) a nucleotide having a 6-substituted 9H-purin-9-yl group as a base; and
    ii) a nucleotide having a 5-substituted-2-oxo(1H)pyridin-3-yl group as a base, whose 5-position is attached either directly or through a linker to a fluorescent dye selected from the group consisting of 5-carboxyfluorescein (5-FAM), 6-carboxyfluorescein (6-FAM), 5-carboxytetramethylrhodamine (5-TAMRA), 6-carboxytetramethylrhodamine (6-TAMRA), 5-dimethylaminonaphthalene-1-sulfonic acid (DANSYL), 5-carboxy-2',4,4',5',7,7'-hexachlorofluorescein (5-HEX), 6-carboxy-2',4,4',5',7,7'-hexachlorofluorescein (6-HEX), 5-carboxy-2',4,7,7'-tetrachlorofluorescein (5-TET), 6-carboxy-2',4,7,7'-tetrachlorofluorescein (6-TET), 5-carboxy-X-rhodamine (5-ROX) and 6-carboxy-X-rhodamine (6-ROX).

16. The nucleic acid according to claim 15, which is tRNA, mRNA, antisense DNA or RNA, a ribozyme, an aptamer or siRNA.

17. A method for detecting a stem-loop or hairpin structure formation of a nucleic acid, which comprises:
    1) inducing hybridization between the nucleotide of i) and the nucleotide of ii) in the nucleic acid according to claims 15; and
    2) measuring a change in the fluorescence spectrum.

18. The method according to claim 17, wherein the stem-loop or hairpin structure in the nucleic acid is formed upon binding between the nucleic acid and a target molecule.

19. A nucleic acid incorporating two or more adjacent nucleotides having a 6-substituted 9H-purin-9-yl group as a base, which is prepared by the method of claim 5.

20. The nucleic acid according to claim 19, which is tRNA, mRNA, antisense DNA or RNA, a ribozyme, an aptamer or siRNA.

* * * * *